US008448636B2

(12) United States Patent  
Singh

(10) Patent No.: US 8,448,636 B2
(45) Date of Patent: May 28, 2013

(54) METHODS AND APPARATUS FOR SAFE APPLICATION OF AN INTUBATION DEVICE

(76) Inventor: Manu B. Singh, Potomac, MD (US)

( * ) Notice: Subject to any disclaimer, the term of this patent is extended or adjusted under 35 U.S.C. 154(b) by 599 days.

(21) Appl. No.: 12/655,301

(22) Filed: Dec. 28, 2009

(65) Prior Publication Data

US 2010/0163023 A1 Jul. 1, 2010

Related U.S. Application Data

(60) Provisional application No. 61/141,746, filed on Dec. 31, 2008.

(51) Int. Cl.
*A61M 16/00* (2006.01)
(52) U.S. Cl.
USPC ............. 128/202.22; 128/200.26; 128/207.14
(58) Field of Classification Search
USPC ........................... 128/200.26, 202.22, 207.14
See application file for complete search history.

(56) References Cited

U.S. PATENT DOCUMENTS

| 5,361,753 | A  | * | 11/1994 | Pothmann et al. | ....... | 128/207.15 |
| 7,331,346 | B2 | * | 2/2008  | Zocca et al.    | .............. | 128/207.14 |
| 2004/0099263 | A1 | * | 5/2004 | Melker et al.   | ............ | 128/200.26 |

FOREIGN PATENT DOCUMENTS

| EP | 0 578 121 A1 | 1/1994 |
| WO | WO 89/07415 A1 | 8/1989 |
| WO | WO 91/16097 A1 | 10/1991 |
| WO | WO 2005/097246 A1 | 10/2005 |
| WO | WO 2008/123934 A1 | 10/2008 |

OTHER PUBLICATIONS

Kumar, S.S., et al., "Over-inflation of the tracheal tube cuff: a case for routine monitoring" (Abstract only, p. 37), 22*nd* *International Symposium on Intensive Care and Emergency Medicine*, Brussels, Belgium, Mar. 1, 2002 (121 pp).

"King LT-D™ Airway—Instructions for Use," [online], Sep. 2005, Retrieved from the Internet URL www.kingssystems.com.

Galinski, Michel, et al., "Intracuff Pressures of Endotracheal Tubes in the Management of Airway Emergencies: The Need for Pressure Monitoring,"*Annals of Emergency Medicine*, 47(6), pp. 545-547 (2006).

Seegobin, R.D., et al., "Endotracheal Cuff Pressure and Tracheal Mucosal Blood Flow: Endoscopic Study of Effects of Four Large Volume Cuffs," *British Medical Journal*, 288, pp. 965-968 (1984).

Agro, F., et al., "Current Status of the Combitute™: A Review of the Literature," *Journal of Clinical Anesthesia*, 14, pp. 307-314 (2002).

(Continued)

*Primary Examiner* — Laura Bouchelle
(74) *Attorney, Agent, or Firm* — Hamilton, Brook, Smith & Reynolds, P.C.

(57) ABSTRACT

Intubation is a potentially dangerous invasive procedure with many plausible errors, such as over-inflation of a cuff and insertion of an intubation tube in the wrong lumen, potentially resulting in a patient's internal bleeding, suffocation, or even death. An intubation aide according to example embodiments of the present invention allows intubation of a patient, while eliminating potential injury to the patient, increasing accuracy and reliability of the placement of the intubation tube, and drastically decreasing procedural time. Within moments of insertion of the device into a patient, the medical caregiver knows, with complete certainty, the location of the intubation device without applying traditional time-consuming tasks. Embodiments also provide patient safety, if intubated for a prolonged periods, by regulating an inflation pressure of the cuff. The intubation aide can also be used for training purposes and is ideal for intubation in hospital and field settings.

37 Claims, 17 Drawing Sheets

OTHER PUBLICATIONS

Enlund, M., et al., "The Combitube® for Failed Intubation—Instructions for Use," *Acta Anaesthesiol Scand*, 45, pp. 127-128 (2001).

Hsu, C., et al., "Assessment of a New Method to Distinguish Esophageal from Tracheal Intubation by Measuring the Endotracheal Cuff Pressure in a Porcine Model," *Acad Emerg Med*, 12(12), pp. 1153-1157 (2005).

Gaitini, L., et al., "An Evaluation of the Laryngeal Tube® During General Anesthesia Using Mechanical Ventilation," *Anesth Analg*, 96, pp. 1750-1755 (2003).

Stewart, S., et al., "A Comparison of Endotracheal Tube Cuff Pressure Using Estimation Techniques and Direct Intracuff Measurement," *AANA Journal*, 71(6), pp. 443-447 (2003).

Combcs, X., et al., "Intracuff Pressure and Trachael Morbidity," *Anesthesiology*, 95(5), pp. 1120-1124 (2001).

Hagberg, C., et al., "An Evaluation of the Insertion and Function of a New Supraglottic Airway Device, the King LT™, During Spontaneous Ventilation," *Anesth Analg*, 102, pp. 621-625 (2006).

Krafft, P., et al., "Is It Unethical to Use the Combitube in Elective Surgery Patients?," *Anesthesiology*, 98(4), pp. 1022-1024 (2003).

Davis, D., et al., "The Combitube as a Salvage Airway Device for Paramedic Rapid Sequence Intubation," *Annals of Emergency Medicine*, 42:5, pp. 697-704 (2003).

Bagheri, S., et al., "Esophageal Rupture with the Use of the Combitube: Report of a Case and Review of the Literature," *J. Oral Maxillofac Surg*, 66, pp. 1041-1044 (2008).

Keller, C., et al., "The Influence of Cuff Volume and Anatomic Location on Pharyngeal, and Tracheal Mucosal Pressures with the Esophageal Tracheal Combitube," *Anesthesiology*, 96, pp. 1074-1077 (2002).

Ander, D. et al., "Assessing Resident Skills in the Use of Rescue Airway Devices," *Annals of Emergency Medicine*, 44(4), pp. 314-319 (2004).

Frass, M., Combitube, "The Internet Journal of Emergency and Intensive Care Medicine® ISSN 1092-4051," 5(2) (2001).

Klein, H., et al., "Esophageal Rupture Associated with the Use of the Combitube,"*Anesth Analg*, 85:937-939 (1997).

Portereiko, J.V., et al., "Acute Upper Airway Obstruction by an Over-Inflated Combitube Esophageal Obturator Balloon," *J Trauma*. 60:426-427 (2006).

PCT/ISA/206 Form—Invitation to Pay Additional Fees and, where applicable, Protest Fee and Annex to PCT/ISA/206—Communication Relating to the Results of the Partial International Search Report, for PCT/US2009/006720, mailed Aug. 19, 2010, total of 6 pages.

Notification Concerning Transmittal of International Preliminary Report on Patentability including Written Opinion of the International Searching Authority, dated Jul. 14, 2011, issued in International Application PCT/US2009/006720, 12 pages.

\* cited by examiner

METHODS AND APPARATUS FOR SAFE APPLICATION OF AN INTUBATION DEVICE

RELATED APPLICATION(S)

This application claims the benefit of U.S. Provisional Application No. 61/141,746, filed on Dec. 31, 2008. The entire teachings of the above application are incorporated herein by reference.

BACKGROUND OF THE INVENTION

Intubation is the placement of an intubation tube of an intubation device into a lumen (i.e., trachea or esophagus) of the body of a subject in order to provide ventilation by mechanical or artificial means via the intubation tube. Intubation can be in the form of tracheal intubation, which is the placement of a tube into the trachea of a subject, as well as esophageal intubation, which is the placement of a tube into the esophagus of a subject.

Intubation is a potentially dangerous invasive procedure with many plausible errors when performed improperly. An example of an intubation error is over-inflation of a cuff, where the cuff is an inflatable bulb coupled to an exterior wall of the intubation tube and used to maintain a position of the intubation tube in the lumen. Over-inflation of the cuff can result in a patient's internal bleeding or, potentially, death. Another example of a common intubation error is the insertion of the intubation tube in the wrong lumen, potentially suffocating the patient. Even with proper training, medical caregivers cannot visually inspect which lumen the intubation tube was inserted into, and, under stress of emergency response, the medical caregiver can make an insertion error and injure the subject, sometimes fatally. FIGS. 1 and 2 illustrate the foregoing examples.

FIG. 1 illustrates a first subject 101 requiring an intubation tube to assist in the subject's breathing, e.g., due to a health problem that impairs or stops normal breathing. To aid the subject, a medical caregiver may employ an intubation device 100. The procedure for using a traditional intubation device begins by the medical caregiver's clearing the subject's mouth and airway, if needed, then inserting an intubation tube 105 of the intubation device 100 into the subject's trachea or esophagus, depending of the type of intubation device being used. During insertion, the cuff(s) 110 on the intubation tube 105 are in a deflated state. Once the intubation tube 105 is in an inserted position, the medical caregiver can stabilize a position of the intubation tube 105 by inflating the cuff(s) 110 through use of a pilot cuff 120 by a syringe filled with either air or a liquid. The pilot cuff 120 is connected to the cuff(s) 110 via tubing 125 for manual inflation of the cuff(s) 110. Once the cuff(s) 110 are inflated and have stabilized the position of the intubation tube 105, ventilation via the intubation tube through use of a ventilator 102 can begin. As mentioned above, over-inflation of the cuff(s) may result in complications, and the complications may manifest themselves as mucosal bleeding and ischemia, esophageal or tracheal bleeding, or death.

FIG. 2 illustrates a second subject 201 also requiring intubation, in which an intubation tube 205 of an intubation device 200 has been inserted into a lumen. In this example scenario, the intubation tube 205 has been inserted into the incorrect lumen 220, which can result in suffocation of the patient, as well as other complications, including death (see von Goedecke et al. (2007) Anesth Analg, 104:481-483; and ACLS: Principles and Practice. pp. 135-180. Dallas: American Heart Association, 2003) as the resuscitation provided to the patient through use of a ventilator 202 would enter the epigastrium rather than the lungs of the subject.

Current methods and devices used for confirming correct tube placement of the intubation device include: visualization of chest movement during ventilation, sound detection of auscultation of chest and epigastrium, checking for fogging of the intubation device, absence of stomach contents in the device, colorimetric end tidal $CO_2$ detection, waveform capnography, self-inflating esophageal bulb, and pulse oximetry. Verification of cuff inflation level is generally not checked, as the maximal volume of the cuff is generally used and presumed to be accurate.

In addition to unaided visual verification, image sensor systems that employ fiber optic cameras can be used to verify cuff inflation and proper tube placement. Such image systems are not generally used because they are cost prohibitive and, in most cases, unnecessary. Moreover, medical caregivers would have to carry both intubation devices and image sensor systems whenever responding to an emergency, which would complicate or delay response time.

Unfortunately, each method by itself is neither efficient nor reliable for confirming correct tube placement. Thus, the use of multiple methods to confirm correct tube placement is currently the standard of care, which delays a medical caregiver from providing treatment to the subject, possibly leading to unintended injury to the subject.

SUMMARY OF THE INVENTION

An embodiment of the present invention assists medical caregivers by indicating which lumen, esophagus or trachea, an intubation tube has been inserted. Another embodiment assists medical caregivers by controlling a level of inflation of a cuff while the medical caregiver is securing the intubation tube in a lumen. Another embodiment includes a combination of each. The term "medical caregiver" as used herein refers to doctors, emergency responders trained in medical procedures, or persons untrained in medical procedures but who are acting in that capacity with regard to intubation of a subject requiring same, as described herein.

The embodiments may employ an intubation aide that optionally can be attachable to the intubation tube. The combination, including other standard intubation tube components (e.g., cuffs) may be referred to herein as an intubation device. The intubation aide may include a chassis with display elements (e.g., pressure meters, light emitting diodes (LEDs), and audio speakers), pump, pressure valve, sensor, and circuitry to perform configured functions, such as to indicate which lumen the intubation tube has been inserted and control a level of inflation of the cuff. The aide may also include memory and data networking elements to store or report states of the intubation device or accept remote commands to control states of the intubation device.

For purposes of explanation herein, pressure and force measurements, sensors, and related elements or techniques are used interchangeably, both in terms of the pressure or forces inside and outside the cuffs.

The pump, tubing, and cuff form an air-tight (i.e., closed) inflation system that accurately maintains pressure in the cuff once the cuff is inflated. The sensor can include a pressure sensor located anywhere within the air-tight inflation system and report the pressure in a human- or machine-readable form, optionally as "go" or "no go" discrete states or as an actual pressure reading. Alternatively, the pressure sensor may be located on the surface of the cuff (external from the air-tight inflation system) and report the force exerted by the cuff against a wall of the lumen. The pressure sensor may also be sealed in a medical grade sealant when located on the surface of the cuff to prevent direct contact with the lumen. A processor or circuitry may be employed to use the pressure reading to control the pump to inflate the cuff to a level that secures the intubation tube but does not injure the patient.

With regard to indicating which lumen the intubation tube has been inserted, embodiments of the present invention measure an amount of force exerted on the fore of a cuff, an amount of force exerted on the aft of the cuff, or both, while the cuff is inflated or being inflated. In embodiments with fore and aft force measurements of the cuffs, which approximately corresponds to forces also being applied to the anterior and posterior walls of the trachea or esophagus for purposes of explanation herein are being used interchangeably, a differential between the fore and aft forces may be calculated (i.e., anterior minus posterior force measurements), where a positive differential indicates that the intubation tube is located in the trachea and a negative differential indicates that the intubation tube is located in the esophagus. The lumen in which the intubation tube corresponding to the differential calculated may be identified to the responder in an audible, visual, or other human-recognizable format. In an alternative embodiment, a single anterior, posterior, or internal cuff pressure measurement can be made with a comparison of the measurement against an absolute (rather than differential) threshold being used to determine in which lumen the intubation tube has been inserted.

At least one pressure sensor transducer, such as a piezoelectric transducer which generates a voltage as a function of pressure, may be used to measure the amount of pressure exerted on the fore of the cuff, the aft of the cuff, or both. A placement analyzer may be used to measure and analyze the pressures and report a result to a medical caregiver. It should be understood that force sensors may be employed to measure force at specific locations and that the force is a function of the pressure.

Additional methods and apparatuses relate to controlling inflation of cuff(s) coupled to an intubation tube of an intubation device. Responsive to an activation signal, such as an electrical boolean TRUE signal generated by a medical caregiver's pressing of a "start" button, inflation of the cuff(s) may commence. A pump inflates the cuff(s) via a pilot cuff tubing. In this embodiment, the pressure indication inflation of the cuff(s) is monitored, and a deactivation signal is generated as a function of a level of the inflation, where the pressure measured is compared against a threshold, range, or other parameter and the deactivation signal is generated once the proper pressure has been reached. Responsive to the state of the deactivation signal, the inflation of the cuff(s) is either continued or discontinued. The amount of inflation is set such that injury to the subject undergoing intubation does not occur, while adequately securing the cuff(s). Redundant sensing, such as force sensing as described above, may also be employed. It should be understood that the activation and deactivation signals, which may be analog or digital, or electrical or optical, may be the same signal or different signals.

Generation of the deactivation signal, such as due to cuff overpressure or incorrect insertion of the intubation tube, may be based on the pressure exerted on at least one pressure sensor transducer coupled to the cuff(s) while the intubation tube of the intubation device is within the oropharynx, esophagus or trachea of a subject. Other parameters may be used to deactivate pumping of the cuff(s), such as a time limit being exceeded (e.g., representing a leaky cuff, faulty pump, or overheating of the pump).

Further, the placement analyzer may cause the pump to drive out air if placement of the intubation tube has been detected, thereby rapidly deflating the cuff(s) and allowing the medical caregiver to reinsert the intubation tube but into the correct lumen. For example, if the intubation tube is designed for esophageal intubation and the measured forces indicate that the intubation tube is located in the trachea, the placement analyzer generates a characterization signal (e.g., sound or light) to alert an medical caregiver to remove and reinsert the intubation tube until the location of the intubation tube is characterized as being in the esophagus, which may be indicated to the medical caregiver by a different characterization signal. Alternatively, if the intubation tube is designed for tracheal intubation and the measured forces indicate that the intubation tube is located in the esophagus, the placement analyzer generates characterization signals to alert a medical caregiver to remove and reinsert the intubation tube until the location of the intubation tube is characterized as being in the trachea.

Following notice by the placement analyzer that the intubation tube is in the correct lumen, the medical caregiver may connect a positive pressure ventilator, which is separate from the pump used to inflate the cuff(s) in some embodiments, to the intubation tube and activate the positive pressure ventilator to provide oxygen to the lungs of the subject.

It should be understood that the foregoing example embodiments, or aspects thereof, may be combined in systems, devices, methods, etc. to form various combinations of same.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A-1 is a diagram illustrating an intubation device having a Vital DCDP design inserted into the esophagus of a patient with a positive pressure ventilator attached;

FIG. 3A-2 is a mechanical diagram of an intubation device using a dual-cuff dual-port (DCDP) design (hereinafter Vital DCDP design) having an intubation aide to perform functions according to an embodiment of the present invention;

FIG. 5B-1 is a block diagram of example circuitry employed by a pump controller/regulator according to an example embodiment of the present invention;

FIG. 5B-2 is a schematic flow diagram of a pump controller according to an example embodiment of the present invention;

DETAILED DESCRIPTION OF THE INVENTION

A description of example embodiments of the invention follows. The teachings of all patents, published applications and references cited herein are incorporated by reference in their entirety.

Figures 1, 3A:
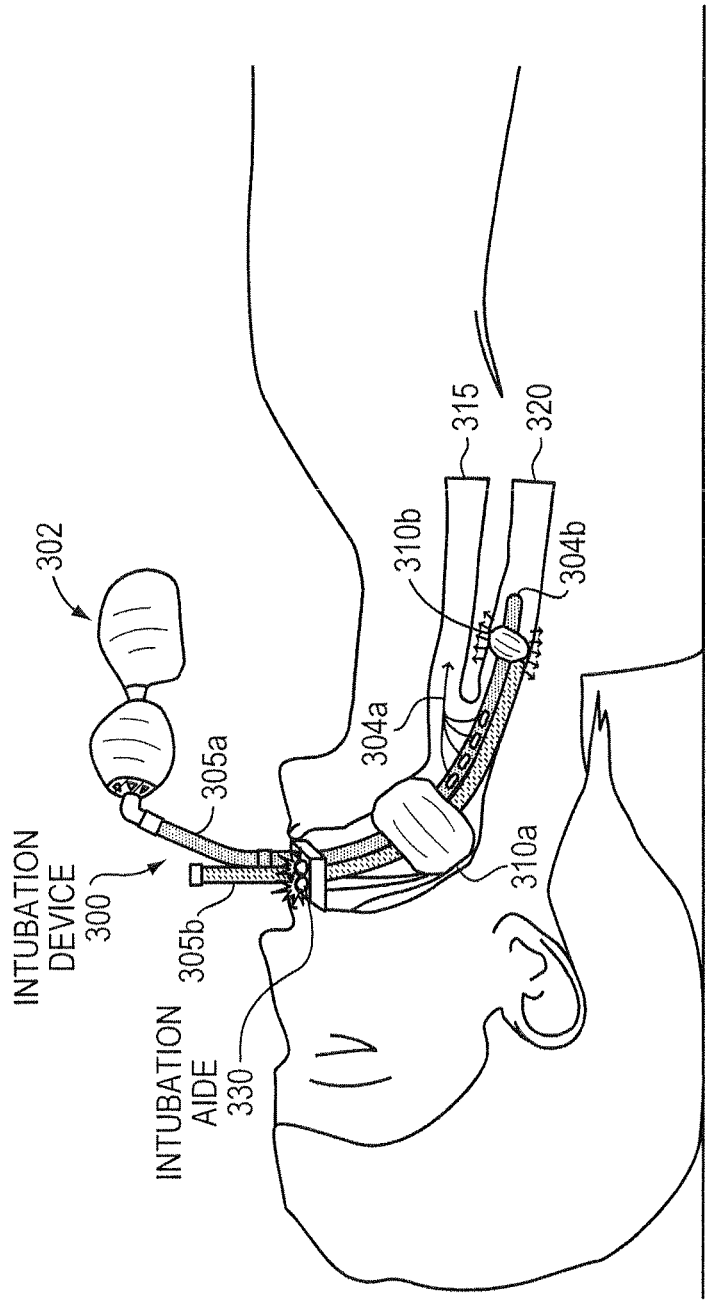
Figures 2, 3A:
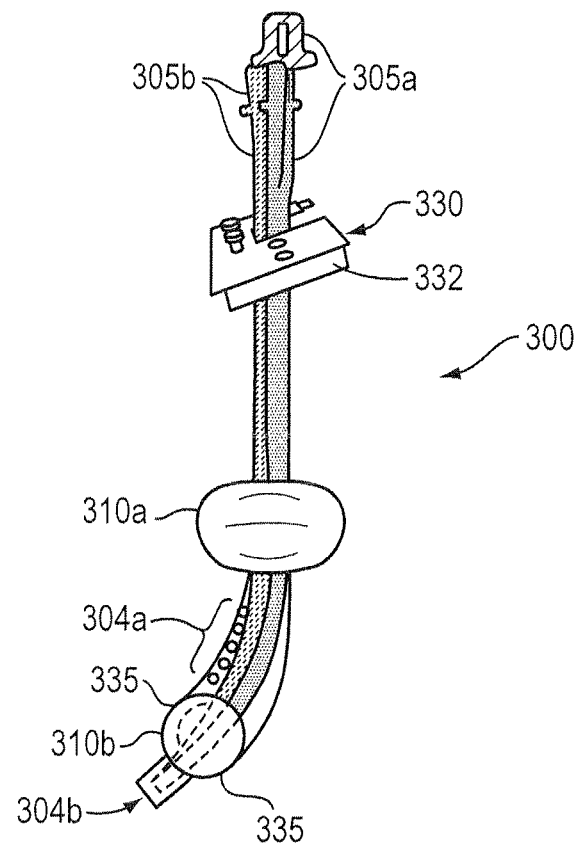
Figure 3B:
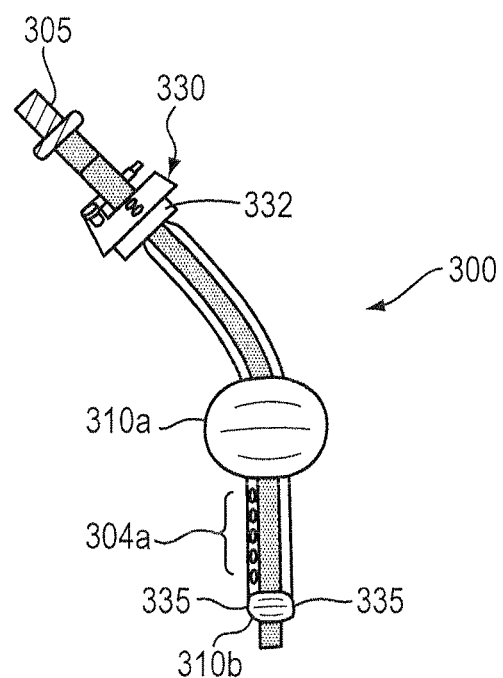
FIG. 3B is a mechanical diagram of an intubation device using a dual-cuff single-port (DCSP) design (hereinafter Vital DCSP design) having an intubation aide to perform functions according to an embodiment of the present invention.
Figure 3C:
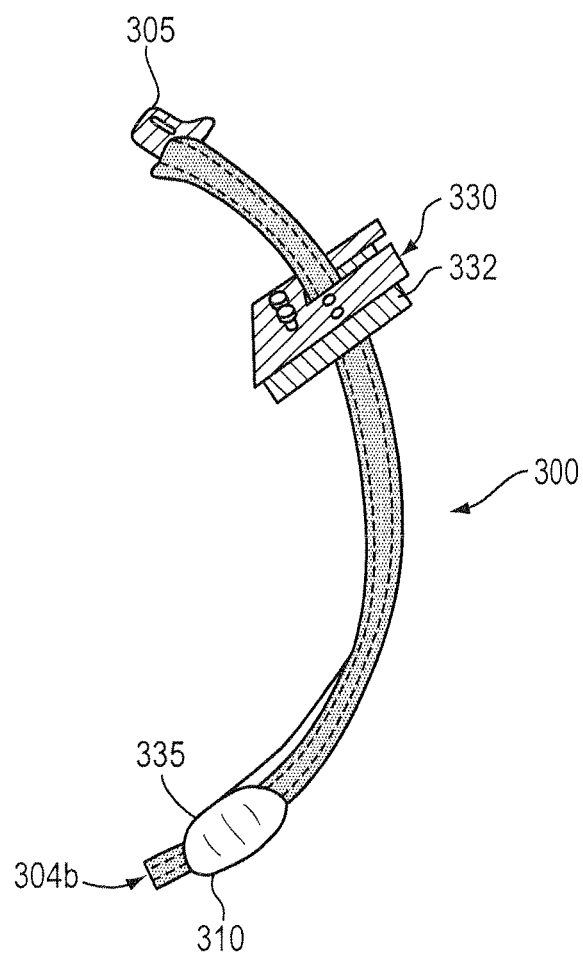
FIG. 3C is a mechanical diagram of an intubation device using a single-cuff single-port (SCSP) design (hereinafter Vital SCSP design) having an intubation aide with apparatus therein to perform functions according to an embodiment of the present invention.

FIGS. 3A-C illustrate designs of intubation devices that may be employed with embodiments of the present invention.

Figure 1:
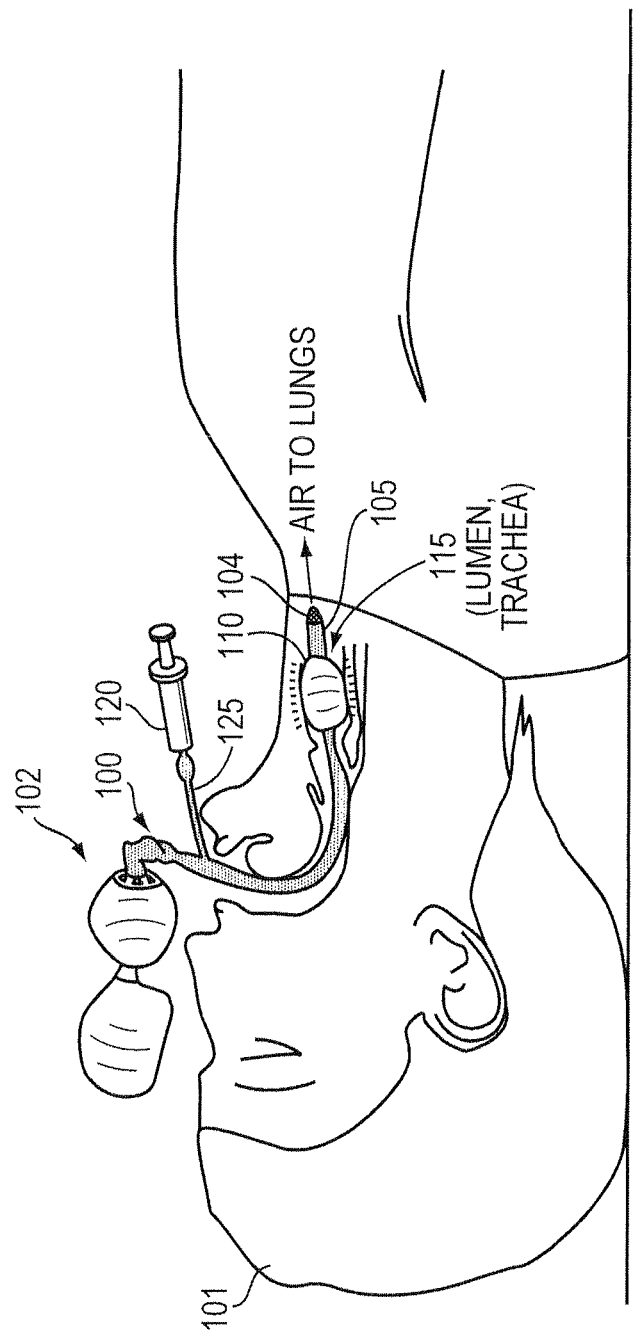
FIG. 1 is a diagram of a prior art intubation tube illustrating over-inflation of a cuff, coupled to an intubation tube, located in the proper lumen of a body, appropriate for the intubation device.

FIG. 3A-1 is a diagram illustrating an intubation device 300 having a Vital DCDP design with at least one intubation tube 305a, 305b inserted into an esophagus 320 of a patient. The Vital DCDP is designed, as illustrated, to be placed into the esophagus 320 or trachea 315 of the patient. The Vital DCDP has side holes 304a aligned with the patients trachea 315 to direct airflow from the intubation tube 305a into the trachea 315, when the intubation tube 305a is placed into the esophagus. Alternatively, the Vital DCDP directs airflow from the intubation tube 305b to the trachea 315 via hole 304b, if the intubation tube 305b is placed in the trachea 315. After the intubation device 300 is inserted, a medical caregiver may begin ventilation of the patient using a ventilator 302. The ventilator 302 is attached to the intubation device 300 to transfer air into the trachea 315 of the patient. During ventilation, the proximal cuff 310a prevents back flow of air, ensuring that a maximal amount of air is transferred into the trachea 315 while also securing the location of the intubation tube 305a.

In the past, the medical caregiver has only been able to confirm correct tube placement of the intubation device 300 after beginning ventilation. Examples of confirming correct tube placement using traditional methods include visualization of chest movement during ventilation and sound detection of auscultation of chest and epigastrium, among others. Embodiments of the present invention include an intubation aide 330, which allows a medical caregiver to confirm tube placement of the intubation device prior to beginning ventilation of the patient. The intubation aide 330 is able to determine the placement of the intubation device by detecting forces exerted on a distal cuff 310b then alerting the medical caregiver of the location of the intubation device 300. By determining placement of the intubation device prior to ventilation, a number of possible injuries to the patient can be avoided. Further, control of cuff inflation can be performed by the intubation aide 330, thereby avoiding other possible injuries.

For purposes of discussion, the intubation aide 330 may refer to all or a subset of components or corresponding methods used to aide a medical caregiver in pre-ventilation activities, active resuscitation, or on-going ventilation activities. Examples of intubation aides 330 include pumps, electronics, sensors (including transducers), status indicators, and communications modules, which are described in more detail below.

Intubation devices, having a cuff, may have a single or double lumen design, along with a dual-cuff dual-port design, referred to as a Vital DCDP design herein (e.g., a resuscitation tube design), a dual-cuff single-port design, referred to as a Vital DCSP design herein (e.g., a transpharyngeal tube design, a laryngeal tube design), and a single-cuff single-port design, referred to as a Vital SCSP (e.g., a laryngeal mask airway, an endotracheal tube design). Regardless of the design, the intubation tube(s) are configured to be inserted into the trachea or esophagus to provide ventilation of a subject (e.g., an injured person or animal). The cuff is inflated through use of a pilot cuff and is used to maintain a position of the intubation tube in the trachea or esophagus of the subject.

Example embodiments of the present invention are directed to confirming proper placement of an intubation tube through monitoring force(s) between an inflatable cuff and an interior of a lumen. Alternative example embodiments of the present invention are directed to inflating a cuff to a desired pressure. Other example embodiments are related to recording, controlling, testing, or calibrating intubation devices.

Embodiments also monitor patient safety, as cuffs alter their pressure after prolonged placement in a patient, often injuring the patient. The intubation aide can also be used for training purposes and can be employed with intubation in hospital and emergency field settings.

Figure 2:
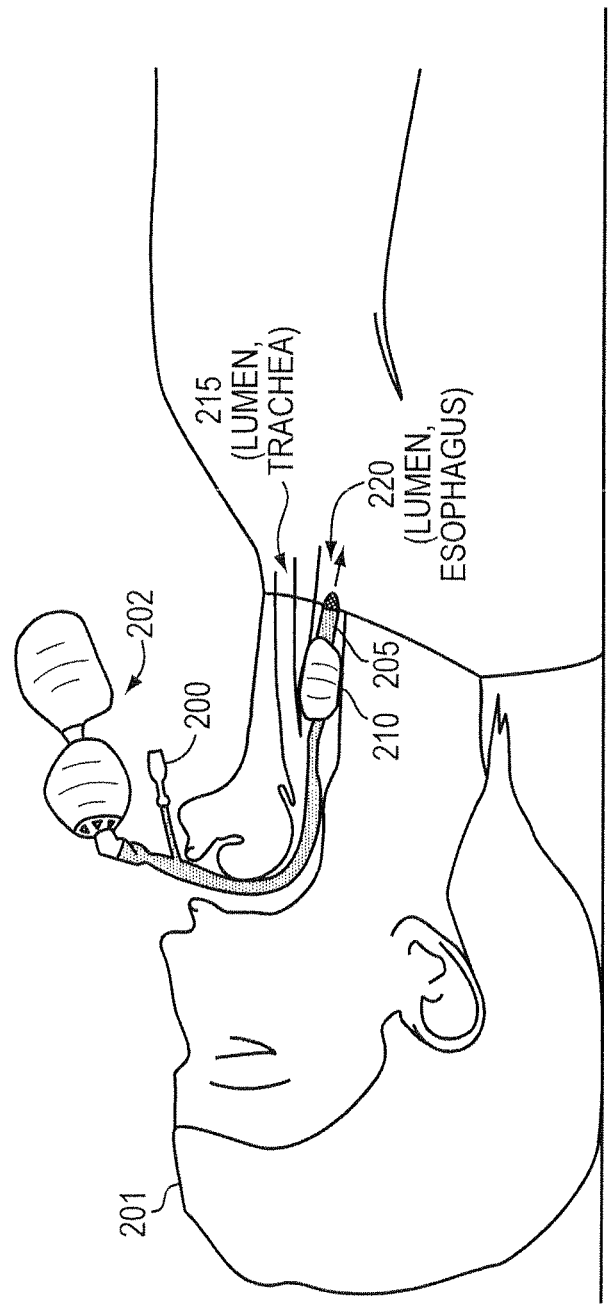
FIG. 2 is a diagram of a prior art intubation device illustrating insertion of an intubation tube into an incorrect lumen (e.g., esophagus instead of trachea)

FIG. 3A-2 illustrates a Vital DCDP intubation device 300 with a double lumen design. The Vital DCDP intubation device 300 with two intubation tubes 305a, 305b may include an intubation aide 330 with a chassis 332 attachable to the tubes 305a, 305b, a proximal cuff 310a, and a distal cuff 310b. A first tube 305a allows resuscitation when placed in the esophagus by way of a side opening(s) 304a, and a second tube 305b allows resuscitation when placed in the trachea or esophagus by way of an opening 304b at the distal end. In addition, at least one pressure or force transducer 335 is coupled to an external wall of the distal cuff 310b and in operative communications with electronics (not shown) of the intubation aide 330 in the intubation assistance chassis 332. The term "transducer" as used herein refers to a specific element, such as a piezoelectric element, that generates an electrical signal, such as a voltage, as a function of forces or pressure, and the term "sensor" includes a transducer and electronics that performs functions on the electrical signal generated by the transducer. Details of how the electronics and transducer operate together are described below beginning in reference to FIG. 4A.

FIG. 3B illustrates an intubation device 300 having a Vital DCSP design. The Vital DCSP intubation device 300 with intubation tube 305 may include an intubation aide 330 attachable to the tube 305, a proximal cuff 310a, and a distal cuff 310b. The tube 305 allows resuscitation when placed in the esophagus or trachea by way of a side hole or holes 304a. In addition, at least one pressure or force transducer 335 is coupled to an external wall of the distal cuff 310b and in operative communications with electronics (not shown) in the intubation aide 330.

FIG. 3C illustrates an intubation device 300 having a "Vital SCSP design." The intubation device 300 with intubation tube 305 may include an intubation aide 330 attachable to the tube 305 and single cuff 310. The tube 305 allows resuscitation when placed in the trachea by way of a distal opening 304b. In addition, at least one pressure or force transducer 335 is coupled to an external wall of the cuff 310 and in operative communications with electronics (not shown) in the intubation aide 330.

The intubation devices 300 of FIGS. 3A-C also include cuff inflation port(s) or pilot cuff port(s) (not shown) used to inflate the cuff(s). The pilot cuff port(s) may be located within the intubation aide 330. Further, the number of ports does not always correspond to the number of cuffs; for example, one port can be used for more than one cuff, as illustrated by the Vital DCSP design.

Figure 4A:
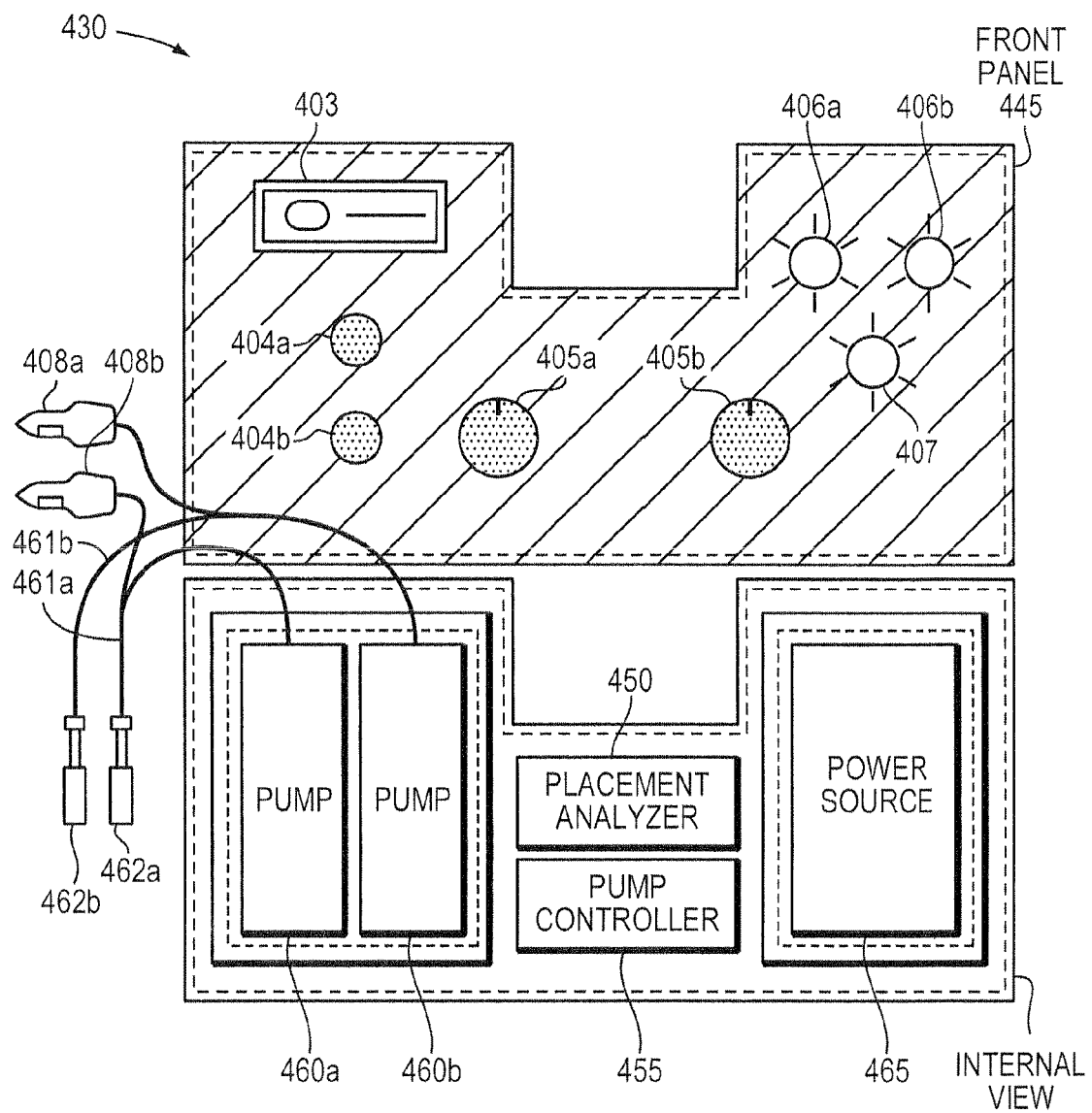
FIG. 4A is a schematic diagram of an intubation aide for an intubation device having a Vital DCDP design.
Figure 4B:
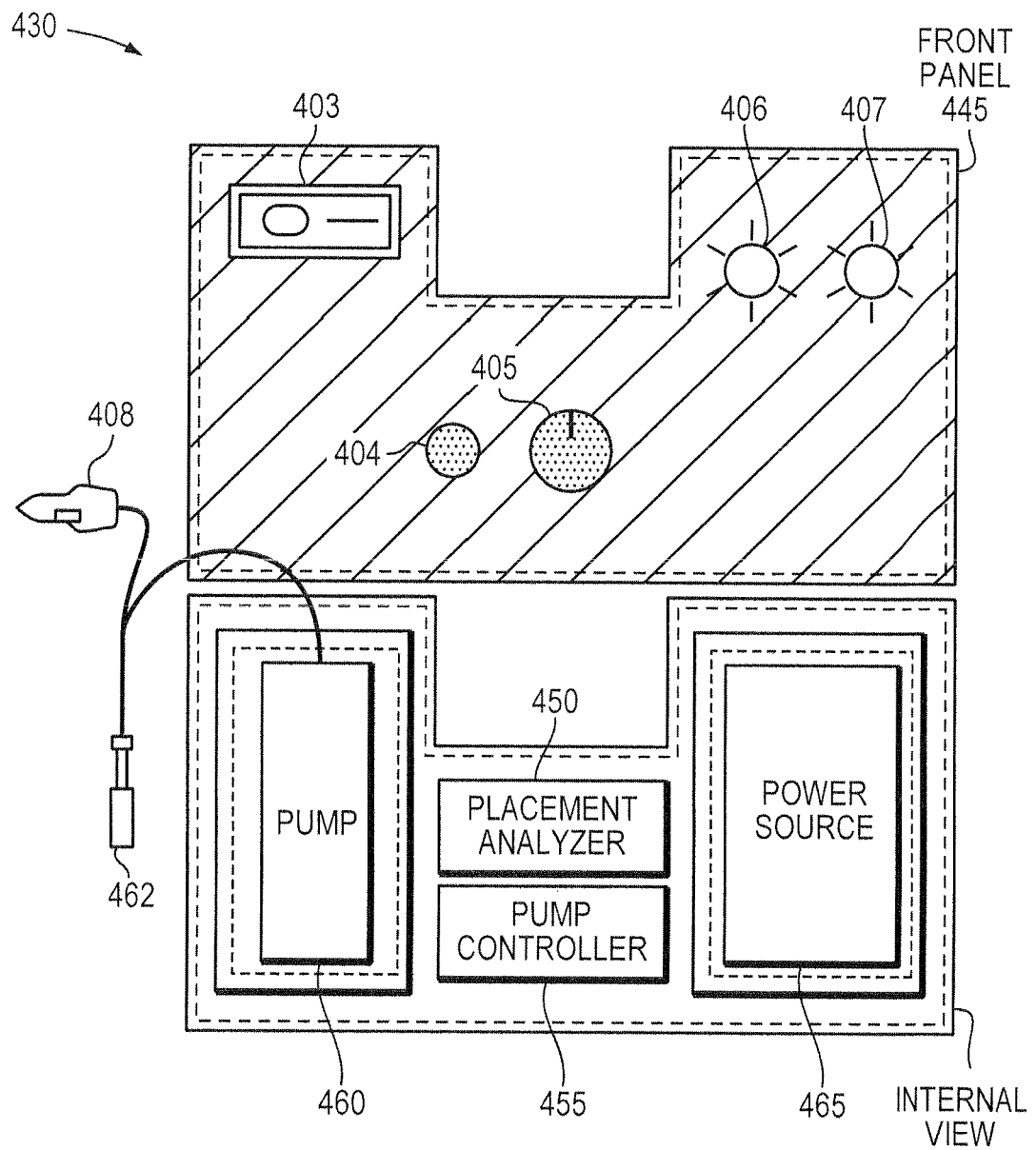
FIG. 4B is a schematic diagram of an intubation aide, including a pump controller and placement analyzer, for an intubation device having either a Vital DCSP or Vital SCSP design, as the device is applicable to all intubation designs with a single port.
Figure 4C:
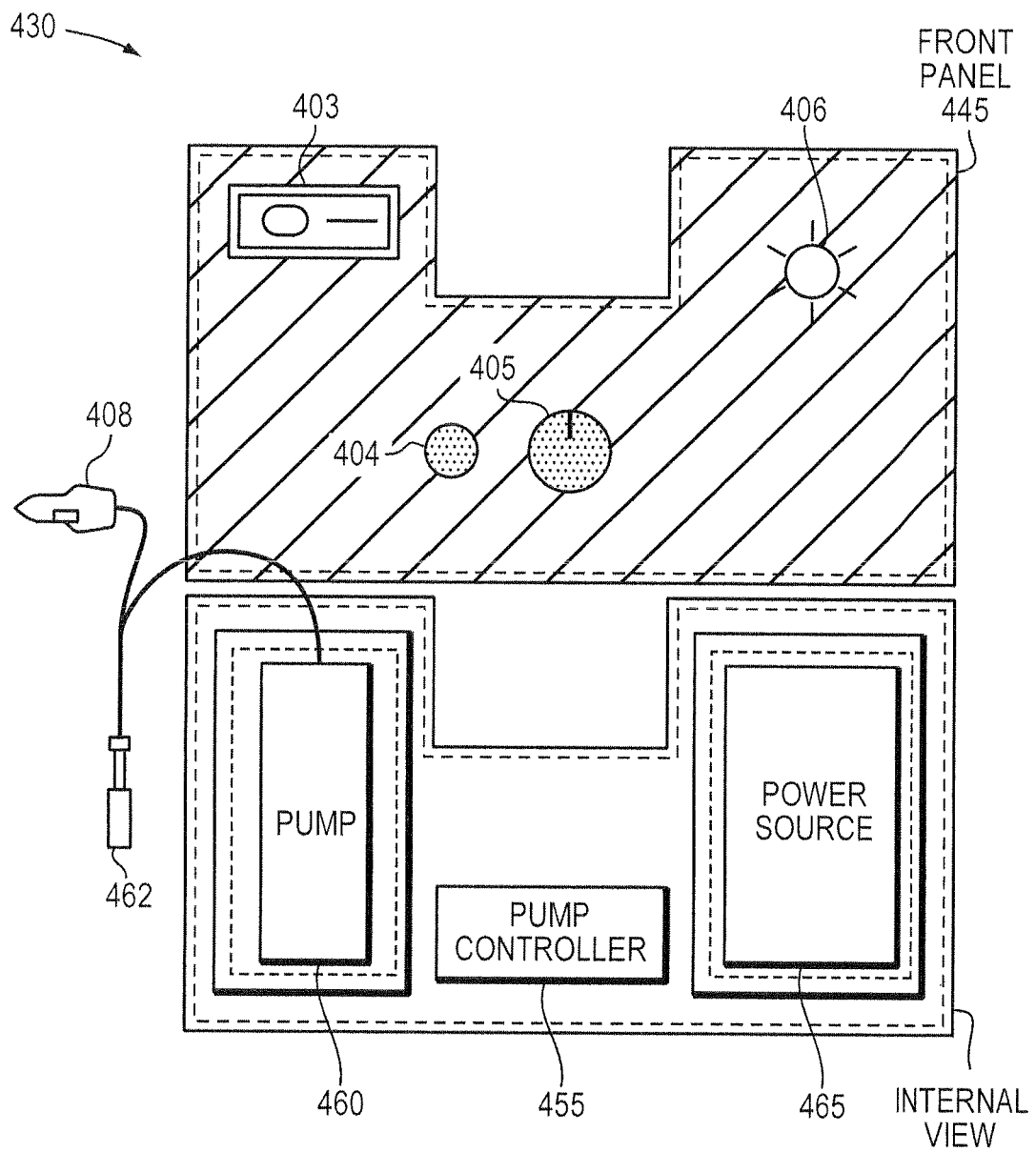
FIG. 4C is a schematic diagram of an intubation aide, including a pump controller, for an intubation device having either a Vital DCSP or Vital SCSP design, as the device is applicable to all intubation designs with a single port.

FIGS. 4A-4C are schematic diagrams of intubation aide designed for intubation devices having a Vital DCDP, Vital DCSP, or Vital SCSP designs, respectively. As illustrated in FIGS. 4A-4C, each intubation device may have its own respective intubation aide with associated front panel to provide for the intubation device's proper functionality.

FIG. 4A is a schematic diagram illustrating an intubation aide ("apparatus") 430 configured for a dual-port intubation device (i.e., Vital DCDP design). The apparatus 430 includes a front panel 445 and internal functional elements (e.g., pumps 460a, 460b, power source 465) controlled or activated by human-to-machine interface elements on the front panel 445.

In this example embodiment, the apparatus 430 includes a placement analyzer 450 and pump controller 455 used to perform functions as described below. The apparatus 430 further includes pumps 460a and 460b with respective output tubes and cuff ports 462a, 462b. The pilot cuff ports 462a, 462b are configured to connect to their corresponding cuffs (not shown) and to the pumps to allow the cuffs to be inflated. The apparatus 430 further houses a power source 465, which may be any form of portable power, such as a battery.

The front panel 445 also includes an on/off switch 403 to power on/off the intubation device, such as by electrically activating the placement analyzer 450 and pump controller 454, and arming the pumps 460a, 460b, which are manually triggered in some embodiments by a medical caregiver by way of pushbutton trigger switches 404a, 404b configured to activate the placement analyzer 450 and pump controller 455, which, in turn, activates the pumps 460a, 460b for each cuff. The front panel 445 may also include knobs 405a and 405b configured to enable the medical caregiver to set user-adjustable pressure for each cuff. Alternatively, the knobs 405a, 405b may not be provided to prevent medical caregivers from accidentally over-inflating the cuffs; instead, a factory setting or calibration may be employed with the pump controller being configured to perform field adjustments. The front panel 445 may further include a pressure level display 406a, 406b, configured to indicate a fully-inflated pressure level, and a placement display 407 configured to indicate placement of an intubation tube of the intubation device. Each pump-cuff port connection 462a, 462b may be connected to pressure relief valves 408a and 408b configured to prevent maximal over-inflation of the cuffs.

The front panel 445 and internal electronics, such as the placement analyzer 450 or pump controller 455, may be configured to support additional sensors that are configured to sense correct insertion in a lumen of an intubation tube. An example of sensors that may be used are "body insertion" sensors, such as moisture sensors, body chemistry sensors, temperature sensors, $CO_2$ sensors, and acidity sensors, and also acceleration or other motion detection sensors (e.g., an accelerometer), where the body insertion sensor can be located either on the inside or outside wall of a cuff to detect when the intubation tube has been deployed in a subject's lumen and the motion detection sensor indicates when the intubation tube has reached a state of rest, optionally for a given duration of time (e.g., 10 seconds), indicating that the tube and cuff(s) have been set in place and are ready to be inflated. Because, in some embodiments, the placement analyzer 450 and pump controller 455 are there to protect against incorrect deployment, the medical caregiver has intelligent failsafe protection in case a fully autonomous activation mode incorrectly activates. Moreover, an emergency override button (not shown) may also be provided to deflate the cuff(s) and deactivate all circuitry. Manual access to the pilot cuffs for manual inflation of the cuffs may also be provided for full manual override. The pump controller(s) and/or placement analyzer(s) may also be controlled via a console that remotely (not shown) views the outputs of the Vital design. Examples of remote access or control are described below in reference to FIG. 8.

FIG. 4B-C are a schematic diagrams illustrating an intubation aide 430 configured for a single-port intubation device design (i.e., a Vital SCSP or Vital DCSP). More specifically, FIG. 4B illustrates the aide 430 for a single-port intubation device design that includes both the placement analyzer 450 and pump controller 455. FIG. 4C illustrates the apparatus 430 with only the pump controller 455. The basic operation of the components of the apparatus 430 of FIGS. 4B and 4C is the same as that described in reference to FIG. 4A.

Placement Analyzer

In operation, embodiments of the present invention may measure forces exerted by walls of a lumen (e.g., trachea or esophagus) of a subject on an anterior side and posterior side of cuff(s) during inflation. The measured forces exerted on the cuff(s) may then be used to determine whether the intubation tube of the intubation device is located in the trachea or esophagus. The reason for force differences between the fore and aft of a cuff is due to human and animal anatomy. Specifically, the trachea is bounded on the anterior side by cartilaginous rings but only bound by soft tissue on the posterior side. The esophagus is bounded by soft tissue on the anterior side but adjacent to hard vertebrae along the posterior side. Thus, force differences can be measured anterior and posterior in both lumens during cuff inflation.

As described above in reference to FIG. 3A, pressure or force transducer(s) are coupled to an external wall of a cuff and are in operative communications with electronics (e.g., placement analyzer as illustrated in FIG. 4A) in the intubation aide. The transducer(s) measure forces exerted to the external walls of the cuff and, in some embodiments, communicate the measurements to the placement analyzer. The measurements may also be directed to the pump controller as redundancy to measurements by the pressure sensors that sense pressure within the cuffs, in which case appropriate conversion of force external on the cuffs to pressure internal to the cuffs is performed through hardware, firmware, or software.

According to an embodiment of the present invention, the placement analyzer is used to detect if a force exerted by a wall of the lumen on the fore of the cuff is greater than a force exerted on the aft of the cuff and also to determine the location of the cuff. If the force on the fore of the cuff is greater than the force on the aft of the cuff, the placement analyzer determines that the cuff is located in the trachea of a subject. If, however, the force exerted on the aft side of the cuff is greater than the force exerted on the fore side of the cuff then the placement analyzer determines that the cuff is located in the esophagus of the subject. Upon determination of the location of the cuff, the placement analyzer may indicate the location to a medical caregiver via any human- (or machine-)observable signal, e.g., a digital readout, light, sound, or to an external device. The observable signal indicates the location of the intubation tube of the intubation device, such as whether the intubation tube is located in the trachea or esophagus of the subject.

The placement analyzer may include a combination of electrical components, such as operational amplifiers (op-amps), microcontrollers, transistors, logic gates, capacitors, and/or resistors, which are operably linked to provide the observable result.

Embodiments of the present invention may employ one or more sensors with transducers operably linked to anterior and posterior sides of the cuff where the forces are to be detected and measured. The forces may be detected or measured by pressure sensor transducers, such as piezoelectric sensors, which provide electric outputs that are proportional to the mechanical force exerted thereon. Piezoelectricity is used in many kinds of sensors, such as piezoresistivity in force sensors, piezoelectric crystals in load cells, piezoelectric and piezoresistive transducers in pressure sensors, and the like. The forces may also be detected or measured by fiber optic pressure measurements, pressure transducers, contact sensing, and strain measurements, all of which provide or affect an electric output (e.g., voltage or current) as a function of force. The forces may be detected or measured simultaneously (i.e., in parallel) or consecutively (e.g., multiplexed).

Figure 5A:
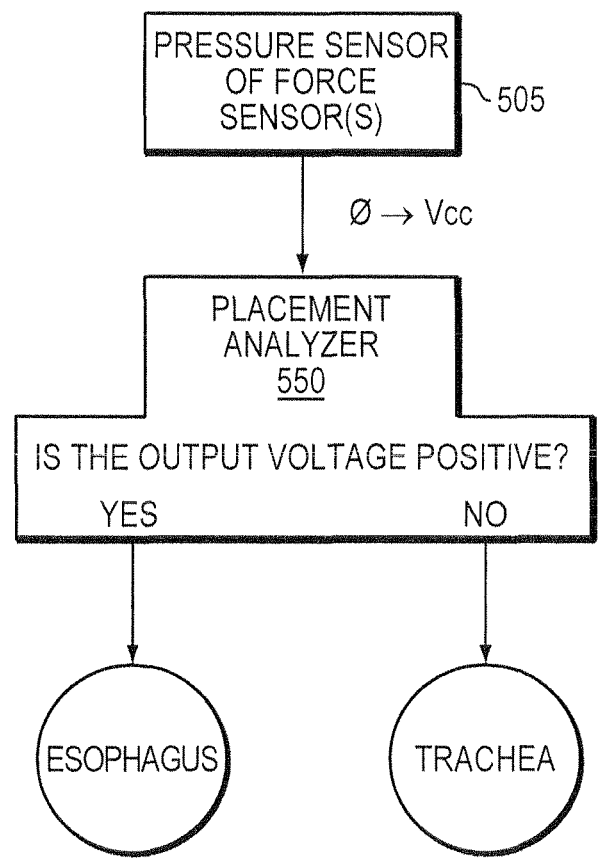
FIG. 5A is a schematic flow diagram of a placement analyzer according to an example embodiment of the present invention.

FIG. 5A is a schematic diagram illustrating a placement analyzer 550. The placement analyzer 500 may employ a single force sensor or multiple force sensors 505 for measuring pressure(s) exerted on at least one sensing area or a pressure sensor measuring the force on the cuff. The placement analyzer 550 receives measurements of forces from the force sensor(s) 505 exerted on an anterior and posterior of a cuff coupled to an intubation tube of an intubation device. The placement analyzer may then calculate a difference between of the forces exerted on the anterior force sensor from the amount of forces exerted on the posterior force sensor. If the result is a positive amount, then the cuff is located in the esophagus of the subject. If the result is a negative amount, then the cuff is located in the trachea of the subject. In alternative embodiments, the force sensors and force analyzer may be implemented such that a positive amount indicates that the cuff is located in the trachea of the subject and a negative amount indicates that the cuff is located in the esophagus of the subject by setting the anterior force sensor to be positive, and the posterior force sensor to be negative. In alternative embodiments, the pump can inflate the cuff for a given duration of time (e.g., 5 seconds), and, if the pressure or force, either inside the cuff or exerted on the cuff, reaches a certain threshold, then the intubation device is determined to be located in the trachea; otherwise the intubation device is determined to be located in the esophagus. Logical changes to polarity of analog signals or corresponding digital signals can be performed, if needed, in analog or digital electronics, or by a programmed processor.

In example embodiments in which the intubation device has a cuff designed to be located in the esophagus, the positive amount may provide a light, such as a green light or another positive signal as an observable result to a medical caregiver. In another example embodiment in which the intubation device has a cuff that is designed to be placed in the trachea, the negative amount may provide a positive signal indicating the cuff is located in the trachea. Alternatively or in combination with the positive signal, a red light or negative signal may be provided to indicate that the cuff is located in the incorrect lumen of the subject for which the intubation device was designed. For example, if the intubation device has a cuff that is designed to be located in the esophagus, a negative signal may be provided as the observable result if the cuff is erroneously located in the trachea of a subject.

Alternatively, a single force sensor can be placed on either the anterior or posterior side of the at least one cuff. The differences between the differential measurements and single measurement is in calculations and having to pre-characterize or quantify forces expected to be observed, which will be different for soft tissue between the trachea and esophagus, ribbing at the anterior of the trachea, and vertebrae at the posterior of the esophagus.

Pump Controller

As described above in reference FIG. 4A, a pump controller may be employed to control inflation of a cuff to a desired pressure, force, or volume. Similarly, the pump controller may be employed to regulate and/or change the pressure, force, and/or volume of the cuff. The desired pressure, force, or volume may be one that provides a seal between the cuff and walls of a lumen (e.g., trachea or esophagus) of a subject without excess pressure or force being applied to the walls of the lumen such that a suitable airway for ventilation via the intubation tube may be maintained. The desired volume may be a preset volume that the cuff is set to not exceed. A pressure relief valve may be connected to the cuff to prevent over-inflation by allowing the release of air if the pressure the cuff exceeds a maximal pressure.

The pump controller may accept inputs from a pressure sensor, timer, force sensors or corresponding placement analyzer, and pump optionally configured with a pressure relief valve(s). It should be understood that combinations thereof, including fewer or more elements providing inputs to the pump controller, may be employed in various embodiments.

The timer may be used to provide a fail-safe against over-inflation of the cuff by providing counts or other metrics, which if exceeded indicate a fault (e.g., leak) in the cuff or tubing associated with the cuff. For example, the pump controller may control and regulate the volume per unit of time (i.e., rate) at which the pump(s) associated with the cuff pumps a gas or liquid into the cuff. Based on the rate and maximal volume of the cuff, the timer may reach a value that causes the pump to stop inflating the cuff and indicate a fault in the cuff or pump.

Figures 1, 5B:
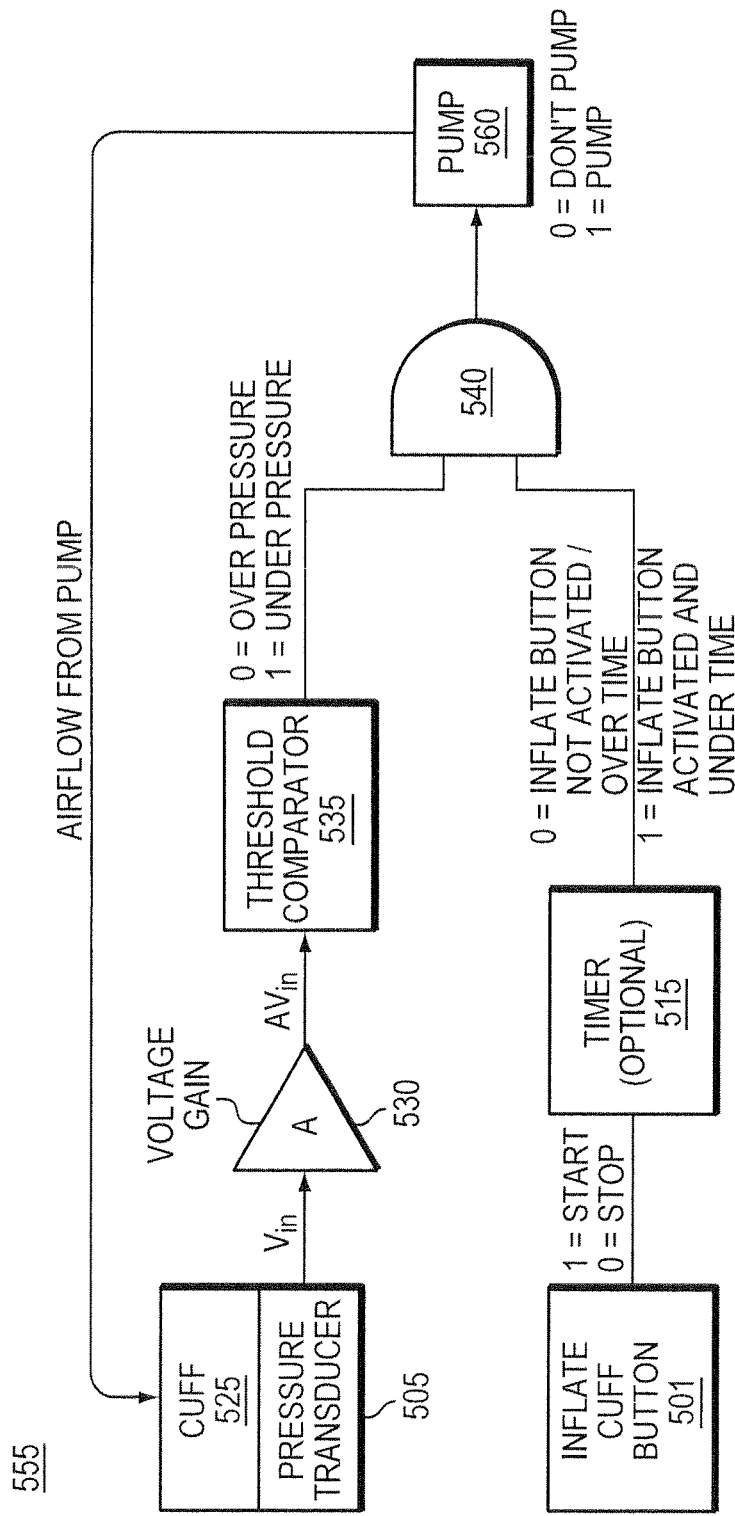
Figures 2, 5B:
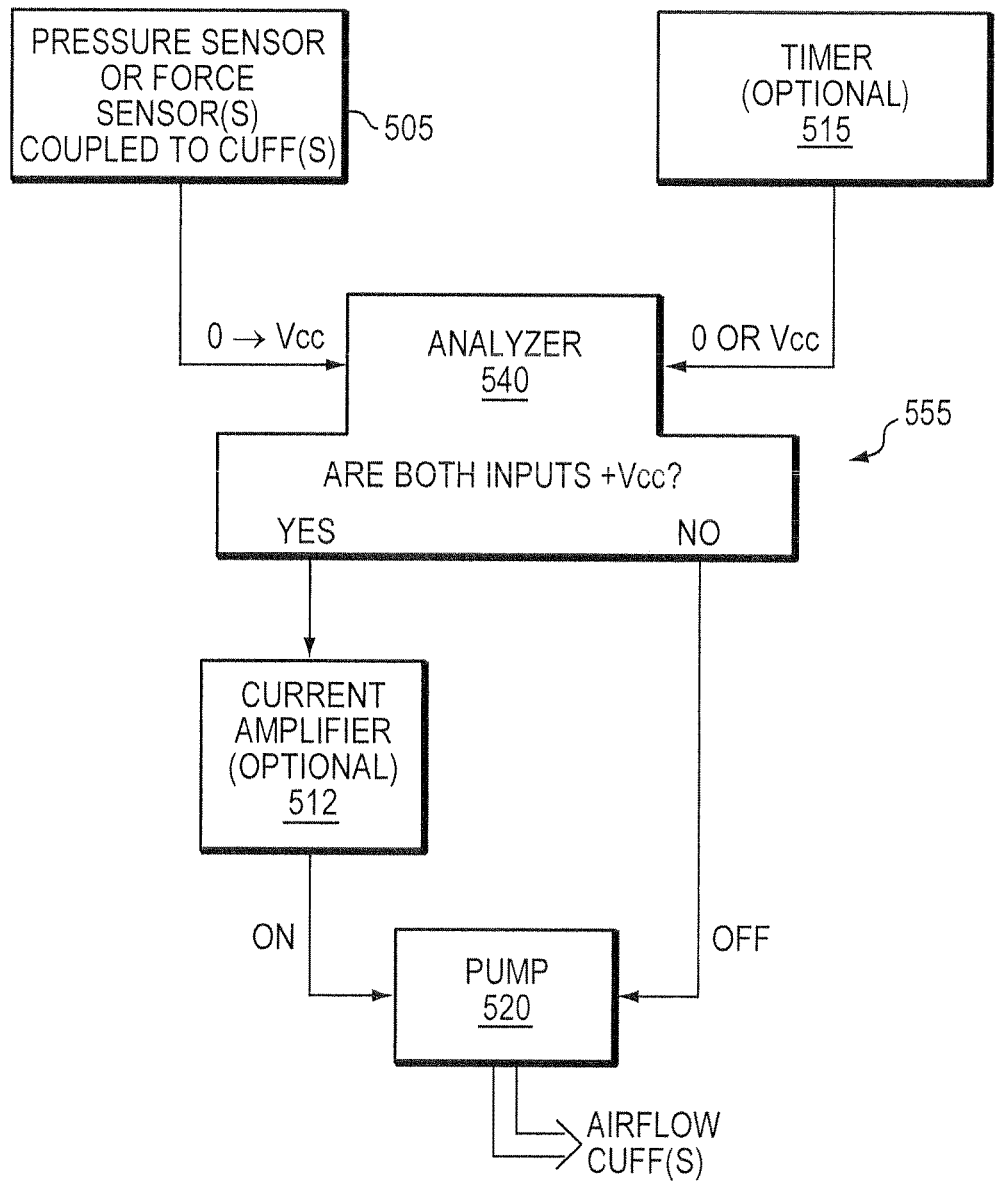

FIG. 5B-1 is a block diagram of an example circuit employed by a pump controller 555 according to an example embodiment of the present invention. Upon insertion of the intubation tube into a lumen of a subject, a medical caregiver begins inflation of the cuff 525 by depressing an "inflate cuff" button 501. Contemporaneously, the depression of the "inflate cuff" button 501 may signal a timer 515 to begin monitoring time elapsed from the time the "inflate cuff" button 501 is depressed. In one embodiment of the fully self-activating system, the "inflate cuff" button 501 may not be present, as the "body insertion" sensor and motion detection sensors indicate insertion and readiness (i.e., tube-is-in-position) states, which can be used to automatically trigger activation of pump(s) to inflate (and deflate) the cuffs, accordingly.

While the cuff 525 is being inflated, pressure transducer(s) 505 measure pressure exerted in the interior of the cuff 525. Based on an amount of pressure measured, the pressure transducer(s) 505 produce an electrical output of voltage $V_{in}$ that is output to a voltage amplifier 530 having a voltage gain, A. The voltage amplifier 530 increases the input voltage $V_{in}$ by effectively multiplying $V_{in}$ by the gain A. The result is an electrical output of voltage $A*V_{in}$ that is output to threshold comparator 535. The threshold comparator 535 determines from the voltage $A*V_{in}$ whether the cuff 525 is over-inflated or under-inflated and produces a digital output of '0' indicating over-pressure, or '1' indicating under-pressure, to an 'AND' gate 540. Contemporaneously, the timer 515 determines whether the "inflate cuff" button 501 is activated and whether the time elapsed since activation is over or under a time threshold. If the "inflate cuff" button 501 is not activated or the timer 515 has exceeded an expected length of time, the timer 515 produces a digital output of '0.' If the "inflate cuff" button 501 is activated and the timer 515 is under-time, the timer 515 produces a digital output of '1' that is output to the 'AND' gate 540.

While receiving the digital output from the threshold comparator 535 and timer 515, the 'AND' gate 540 sends its output to a pump 560 to trigger pumping of the cuff 525. If the 'AND' gate 540 receives a digital '1' from both the timer 515 (pump time not exceeded) and threshold comparator 535 (cuff pressure not exceeded), the pump 560 remains in an active (i.e., pumping) state. If the 'AND' gate 540 receives a digital '0' from either the timer 515 (pump time exceeded (or not started)) or threshold comparator 535 (cuff pressure reached or exceeded), the pump 560 is set into an inactive (non-pumping) state.

It should be understood that all or portions of the example circuit can be implemented in hardware, firmware, or software. In appropriate cases, such as software executed on a processor (not shown), other circuit elements, such as analog-to-digital converters, may be required to allow the processor to process outputs of the sensors.

FIG. 5B-2 is a schematic diagram of a pump controller 555 in accordance with an example embodiment of the present invention. A timer 515 may provide a positive voltage to the pump controller 555 based on a desired time. The desired time may be chosen by a user of an intubation device as a time needed to fill a cuff to a given volume, according to an output of a pump 520. The desired time, given volume, or both, may be selected or adjusted by the user. A pressure (or force) sensor 505 may provide a variable voltage which corresponds to a pressure of the cuff (or the force exerted on the cuff). The pressure (or force) sensor 505 and the timer 515 are analyzed in the analyzer 540 to determine whether or not the pump 520 should be activated. The pump controller 555 may function without the timer, having inflation of the cuff guided by only the pressure or force sensor(s) 505 to fill the cuff. A pressure relief valve (not shown) may function as an additional fail-safe by enabling expulsion of air to maintain a desired pressure level in the cuff in a case in which excess pressure is pumped into the cuff.

Further, the pump controller 555 may provide an electric output to drive the pump 520 based on inputs received from the sensor(s) 505 and timer 515. The pump controller 555 may further include a combination of one or more operational amplifiers (op-amps), microcontroller(s), transistors, capacitors, and/or resistors, which are operably linked to provide an electric output based on inputs. Additionally, the pump controller 555 may also include a current amplifier 512 configured to ensure sufficient current to drive the pump 520; a typical pump that may be used operates at 100-400 mA of current. The pump 520, when activated, may pump a gas, such as air, or a liquid, such as saline, into the cuff. It should be understood that two similar or the same pump controllers 555 may be employed for intubation devices with two cuffs.

Combination of Placement Analyzer and Pump Controller

Figure 5C:
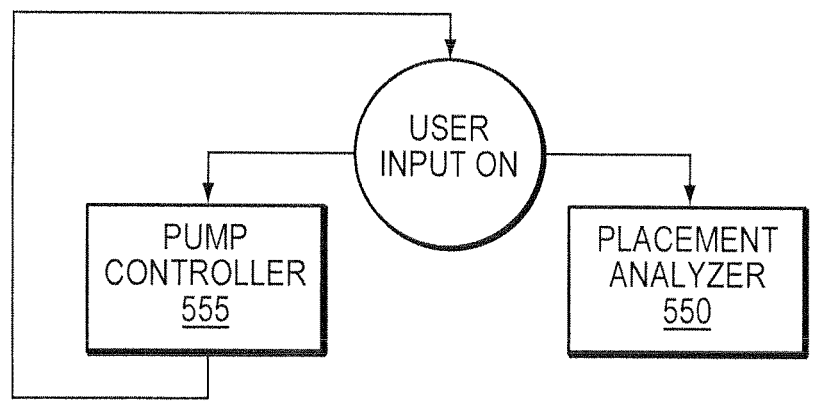
FIG. 5C is a schematic flow diagram of a pump controller connected to a placement analyzer according to an example embodiment of the present invention.

Example embodiments of the present invention may employ a combination of at least one placement analyzer and at least one pump controller. For example, FIG. 5C illustrates a placement analyzer 550 and a pump controller 555, which are simultaneously activated but functionally independent of each other. The pump controller 555 of an intubation device may be designed to turn a pump on or off based upon pressure within the pump. The placement analyzer 550 and pump controller 555 may be integrally connected. For example, a sensor employed in the pump controller 555 of the intubation device may be the same as one or both of the sensors employed in operative connection with the placement analyzer 550.

Figure 5D:
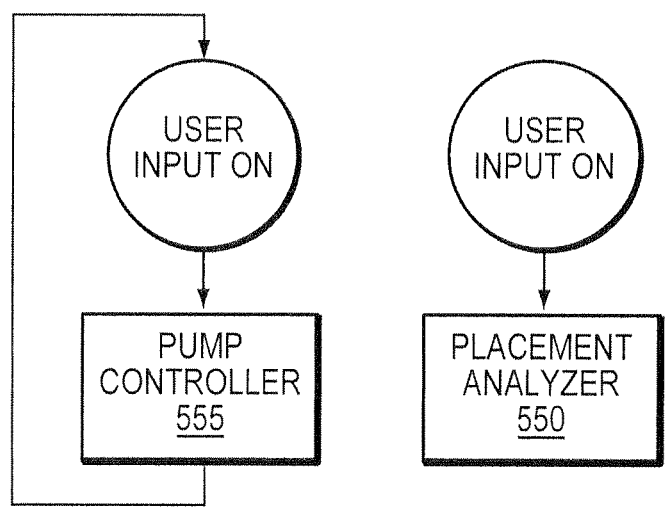
FIG. 5D is a schematic flow diagram illustrating a pump controller and a force analyzer independently operable according to an example embodiment of the present invention.

FIG. 5D illustrates an example embodiment where the placement analyzer 550 and pump controller 555 may be activated independently of each other, e.g., by way of separate ON switches or buttons.

Example embodiments of the present invention may employ an intubation device having a Vital DCDP design, placement analyzer, and pump controller. Pressure or force sensor(s) in a proximal cuff of the intubation device may detect increase in pressure or force of the proximal cuff once the proximal cuff reaches the inside of an aperture, such as the oropharynx, which may then cause a drastic increase in intra-cuff pressure or force (up to 30 cm H2O), thereby stopping a pump. If the pressure or force on the proximal cuff is not sufficient to stop the pump, a timer may then stop the pump after a desired time, e.g., 2.5 seconds.

Alternatively, force sensor(s) in a distal cuff of the intubation device may detect an increase in force on the distal cuff once the distal cuff reaches the inside of a trachea or esophagus of a subject, thereby stopping the pump and indicating a location of the distal cuff.

Increase in pressure or force may indicate that the cuff is located in the trachea. For example, an increase in force or pressure indicates that the cuff is located in the trachea if forces at the fore of the cuff increases at a rate of 20 cm H2O with each ml of air inserted into the cuff, while forces at the aft of the cuff only increases at a rate of 5 cm H2O. More specifically, after the cuff is filled with 5 ml of air, there may be a significant difference in forces exerted between the fore and aft sides of the cuff, as there may be a force of 100 cm H2O exerted on the fore of the cuff compared to a force of 25 cm H2O exerted on the aft of the cuff.

Another example embodiment may employ an intubation device with a Vital DCSP design that may include a placement analyzer and pump controller, as illustrated in FIG. 5C. Pressure sensor(s) in at least one cuff coupled to an intubation tube of the intubation device may be configured to detect increase in pressure of the at least one cuff. A significant increase in pressure may occur once the at least cuff reaches the inside of a lumen. For example, the increase in pressure may be up to 60 cm H2O or 80 cm H2O (if nitrous oxide is used for sedation), as detected by the pressure sensor(s). If the pressure is not sufficient to stop a pump, a timer may be configured to stop the pump after a given time, e.g. 2.5 seconds. The force sensors may also be employed in this example embodiment.

Additional example embodiments may employ an intubation device with a Vital SCSP design that may include a pressure or force sensor(s) coupled to at least one cuff of the intubation device. The pressure or force sensor(s) may be configured to detect increase in pressure or force(s) exerted on the at least one cuff. For example, once the at least one cuff reaches the inside of a lumen (e.g., trachea or esophagus) pressure or force(s) exerted on the at least one cuff may increase (e.g., up to at least 34 cm H2O), thereby stopping a pump. If the pressure or force is insufficient to stop the pump, a timer may be configured to stop the pump after a given time, e.g. 0.5 seconds. As with the distal cuff of the Vital DCDP, in some embodiments, the Vital SCSP may have force sensor(s) in a distal cuff of the intubation device that may be configured to detect increase in force exerted on the distal cuff once it reaches the inside of the lumen. A significant increase in force to one side, fore or aft, of the cuff may cause the pump to stop, which itself may indicate a location of device placement (e.g., trachea or esophagus).

Example Device Configurations

Intubation devices according to some embodiments of the present invention comprise at least one sensor such as a pressure sensor or a force sensor, at least one air pump, connectors, tubing, tubing connectors, air release valve(s), circuitry such as logic gates, microcontrollers, op-amps, transistors, resistors, and the like, a user interface, and a power source such as a battery pack, over-charged capacitor, or lithium, alkaline batteries, or the like.

In some embodiments, the intubation devices of the present invention are portable. In some embodiments, the intubation devices according to the present invention may further comprise operational indicators such as lights, sound speakers, or LCD screen, transmitter to transmit data to an external device, receiver to receive data or commands from an external device, and buttons or switches.

It should be understood that components and corresponding methods beyond basic intubation tube(s) with associated lumen(s) may be part of various embodiments of the intubation aides disclosed herein or equivalents thereof.

Alternative Embodiments

The intubation aide, such as the embodiment illustrated in FIG. 4A, may also include circuitry comprising a breathing monitor, internal memory, use counter, battery monitor, or wireless interface and control unit according to example embodiments of the present invention. The intubation aide may, more generally, be used to track, record, react to, transmit, or take other functional action based on a state of the intubation device, subject being or about to be ventilated, or medical caregiver providing assistance to the subject. Alternatively, the intubation aide may perform actions as a function of a remotely delivered notice or control signal.

As an example, upon successful intubation of a subject and operation of an intubation device, the subject may regain an ability to breathe without the assistance of the intubation device. In such instances, the intubation device may impede the subject's ability to breathe autonomously. As such, the aide may include a breathing monitor configured to detect breathing of a subject and alert the medical caregiver to remove the intubation device. For example, the intubation tube may be internally fitted with a bi-directional flow meter (not shown). A "breathing" analyzer (not shown) can then monitor regularity of artificial breathing for an irregularity, which may indicate the subject is beginning self-breathing capability. The monitoring can be done in the time domain or frequency domain, and many forms of analysis can be employed to monitor for the subject's self-breathing restoration.

As another example, internal memory (not shown) may be configured to record use of the intubation device and any other relevant operational data or device parameters. The memory may record certain information, such as the identity of the medical caregiver that used the intubation device, number of times intubation placement was successful on a first try, not successful on the first try, and number of attempts needed for proper placement of the intubation device. Such information may be used to gather statistics to aid in training of medical caregivers. For example, if the data shows that multiple attempts are needed for correct placement of an intubation device, this may indicate that the medical caregiver needs additional training. Similarly, the data may useful in testing intubation tube designs with different curvatures to determine a curvature that statistically improves placement of an intubation tube in a correct lumen.

The battery monitor may indicate power levels of the battery and signal a need to recharge or replace the battery. The signal may be a local audio or visual signal or may be a wirelessly or wired transmitted signal. A transmitted signal (e.g., voice over IP packet) may include sufficient information for a recipient of the signal to identify the intubation tube and a request, such as a maintenance service request (e.g., battery charging or replacements) that is being notified. Optionally, data providing a location of the intubation device may also be transmitted in the signal.

Figure 8:
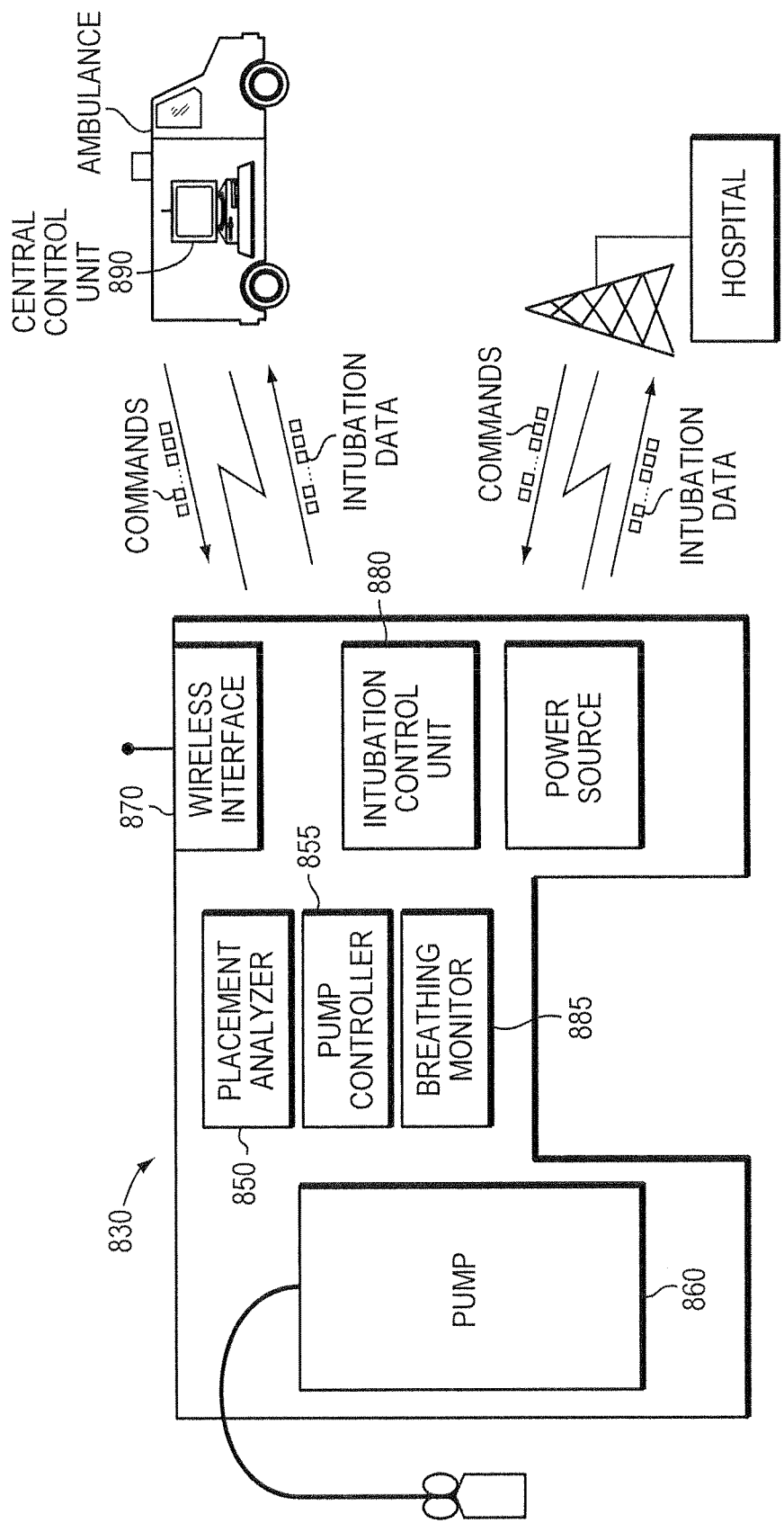
FIG. 8 is a diagram illustrating remote control of an intubation device in accordance with example embodiments of the present invention.

In many emergency situations, a medical caregiver may arrive at a scene where multiple victims need emergency aid. Each of those parties may need the use of an intubation device. In addition, the number of victims may exceed the number of medical caregivers available at the scene. Therefore, a wireless interface and control unit as illustrated in FIG. 8 may be employed to enable remote control of the intubation device by a central control unit or emergency operators at a central emergency operating facility, hospital, or ambulance. The intubation control unit 880 may be configured to allow remote medical caregivers (e.g., doctors) to monitor the intubation device and communicate states to a central control unit 890 via a wireless interface 870. Based on the communication of the states of the intubation device, the central control unit 890 may send commands to the intubation control unit 880 via the wireless interface 870 to cause the intubation control unit to control the circuitry of the intubation aide 830 in a certain manner. For example, the central control unit 890 may command the intubation control unit 880 to shut down operation of the ventilator or cause a valve (not shown) to open to bypass the ventilator if the central control unit has received an indication that the subject has begun unassisted breathing. Conversely, the central control unit 890 may alert the intubation control unit 880 to activate the ventilator (and close the valve if applicable) to begin providing assisted breathing upon detecting no autonomous breathing from the subject.

Figure 9:
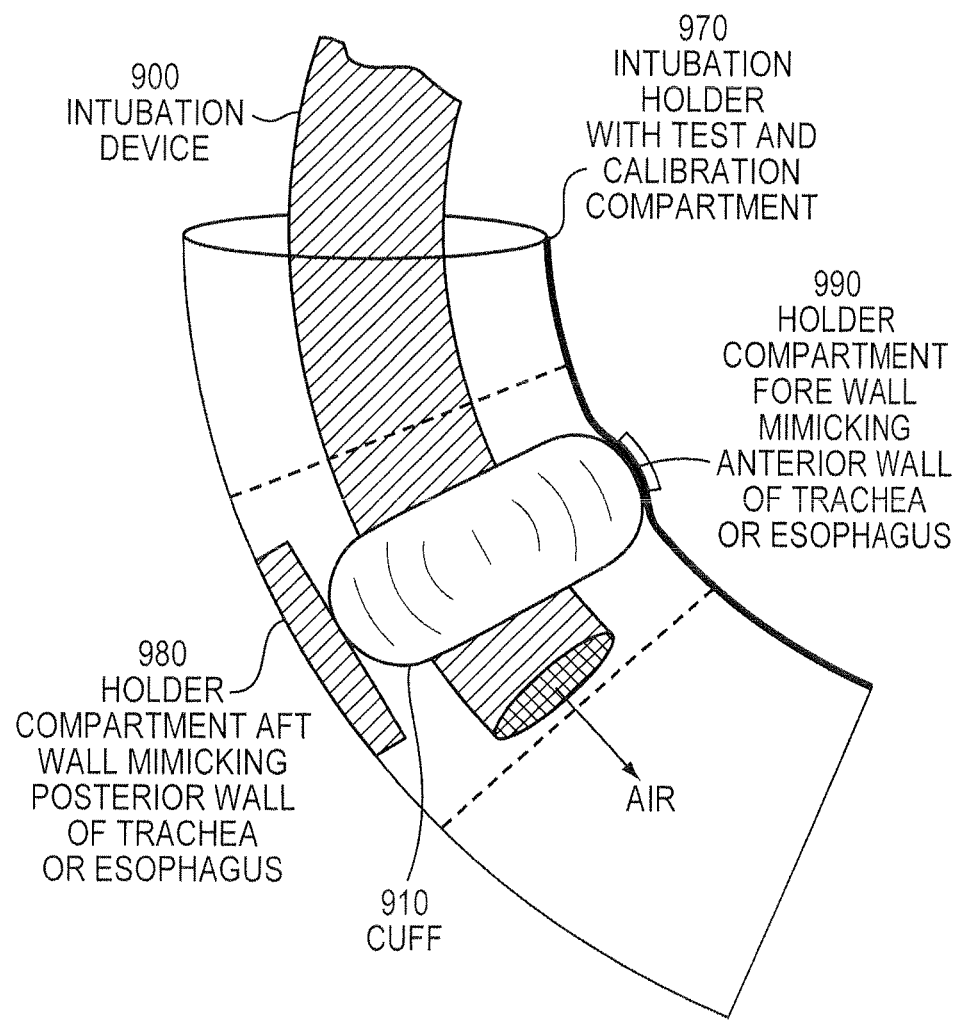
FIG. 9 is a diagram illustrating an intubation device holder with a compartment positioned at each cuff that includes compartment walls designed to biomimic anterior and posterior walls of a trachea or esophagus.

A remote server (not shown) may also cause an intubation aide to run readiness checks (e.g., battery charge state, cuff integrity, etc.) or calibrations on a periodic, random, or event driven basis. For example, the remote server may activate an intubation aide to auto-inflate its cuff(s) a certain length of time and expect to have its pressure sensor report back a measured pressure. If the pressure is higher or lower than expected, the remote server may provide notice to the medical caregiver associated with the intubation device by causing the intubation aide to change a report output to a "fault notification" state, which may include sounding an audible notice, activating a red or blinking LED, or vibrating. Other forms of providing notice include sending a paging message, voice call, voice mail, text message, written notice, or other notice to the medical caregiver to provide notice of a faulty intubation device. Similarly, the remote server may activate the intubation aide to run calibration testing through use of a locally applied biomimicry calibration assembly that mimics a trachea or esophagus with predetermined parameters such that returned or locally stored measurements provide future calibration offsets for making future field uses more accurate and safe. FIG. 9 describes an example calibration assembly.

FIG. 9 is a diagram illustrating an intubation device holder with a compartment positioned at each cuff that includes compartment walls that act as structures designed to biomimic anterior and posterior walls of a trachea or esophagus. The structures may be made of a solid material connected to springs configured with constant spring forces designed to mimic either the anterior or posterior forces of the trachea or esophagus that may be exerted on a cuff. The structures may alternatively be made of a material, such as a foam or rubber, configured to mimic the elasticity of either the anterior or posterior side of the trachea or esophagus. Other structures or materials may be employed to provide the biomimicry structure or function.

Remote (or local) testing or calibration of the intubation aide may also include activating the intubation aide to inflate the cuff(s) 910 while in a specially designed holder 970 with a compartment positioned at each cuff 910 that includes compartment walls 980, 990 designed to biomimic anterior and posterior walls of a trachea or esophagus to test pressure or force sensors configured to measure forces on the fore or aft (or both) of the cuff(s) 910. Because the compartments 980, 990 have predetermined wall stiffnesses, the intubation aide or remote server can be configured to expect certain measurement levels from force or pressure sensors. By knowing the expected measurement levels, the intubation aide may be tested to determine if it accurately determines whether the cuff(s) 910 is located in a trachea or esophagus. Offsets from expected measurements may be stored locally (or remotely) and applied to the intubation aide in a manner making future uses of the intubation aide more accurate. Notifications of faults or downloading of calibration settings or offsets may be transmitted to the medical caregiver, intubation aide, or remote server.

The following examples are intended to illustrate, but not to limit, embodiments of the invention:

Experiment 1

Pump Controller

Step 1a Pressure Sensor calibration: A MPX5050 Integrated Silicone Pressure Sensors was tested with a manometer to verify that the voltage output correctly followed Voltage Output=Vcc*(0.018*Pressure+/−0.04).

Step 1b Force sensor calibration: Tekscan Flexiforce Piezoresistive Force Sensor(s) were calibrated using small weights, measured in increments of 5 grams, and an inverting amplifier, used to verify that it follows Voltage output=−Voltage Input (Fixed Resistance/Flexiforce variable resistance).

Step 2 Pump Controller Analyzer calibration: The pump controller analyzer, employing a comparator, was tested with an input voltage that matched the expected voltage from the pressure or force sensor(s). The analyzer gave an output voltage changing from +Vcc to 0 volts, once the expected voltage was inputted.

Step 3 Pressure or Force Sensors and Pump Controller's Analyzer: The pressure or force sensor(s) were tested together along with the pump controller's analyzer to ensure that there was a 0 voltage output reached at the threshold pressure or force, respectively.

Step 4 Timer circuit Calibration: The pump controller's timer circuit module was tested with an oscilloscope to give an output+Vcc voltage in accordance to the expected designated time. This was done by following the equation: Time=1.1*Resistor*Capacitor in the Monostable Timer Circuit.

Step 5 Pump Controller's Analyzer with the timer circuit and pressure or force sensor(s): The pressure or force sensor(s) along with the timer circuit modules were tested together to ensure that the pump controller analyzer was working correctly. The output voltage of this stage was +Vcc, which would adequately drive the pump, as long as either the pressure or force sensor(s) are below its threshold voltage, and the timer circuit is within its expected time frame, which is dependent on the cuff size. (Otherwise, the output voltage of this stage was 0 volts.)

Placement Analyzer

Step 1 Force sensor calibration: The Tekscan Flexiforce Piezoresistive Force Sensor(s) were calibrated, using small weights of known value and the recommended drive circuit, to verify that it follows its appropriate transfer characteristics. The equation used was: Voltage output=−Voltage Input (Fixed Resistance/Flexiforce variable resistance).

Step 2 Analyzer: The two force sensors were placed in a differential amplifier, which subtracted the voltage output from one force sensor from the other force sensor. This gave a positive or negative voltage output, depending on which force sensor had a higher force against the cuff.

Step 3 Indication: The output voltage of the differential circuit went to two reverse-facing light emitting diodes (LEDs), which would indicate the placement; as one LED was active with a positive voltage input, the other was active (or inactive) with a negative voltage input.

Combination: Pump Controller and Placement Analyzer

The pump controller and placement analyzer were tested together to ensure that they were responsive to increases in pressure and/or force and time. The placement analyzer was tested to ensure that the tracheal and esophageal LED(s) illuminated if the cuff had a higher front force or higher back force, respectively.

Experiment 2

In order to determine the use of this technology in human beings, the following experiment was conducted in an animal model. Pigs were utilized, as they have similar respiratory system to other mammalian species.

Two pigs were utilized in each of the two experiments (Experiment 2A and Experiment 2B). The pigs were initially sedated with Telazol 4.4 mg/kg and Xylazine 2.2 mg/kg, and maintained sedation with 2.00% Isoflurane.

Figure 6A:
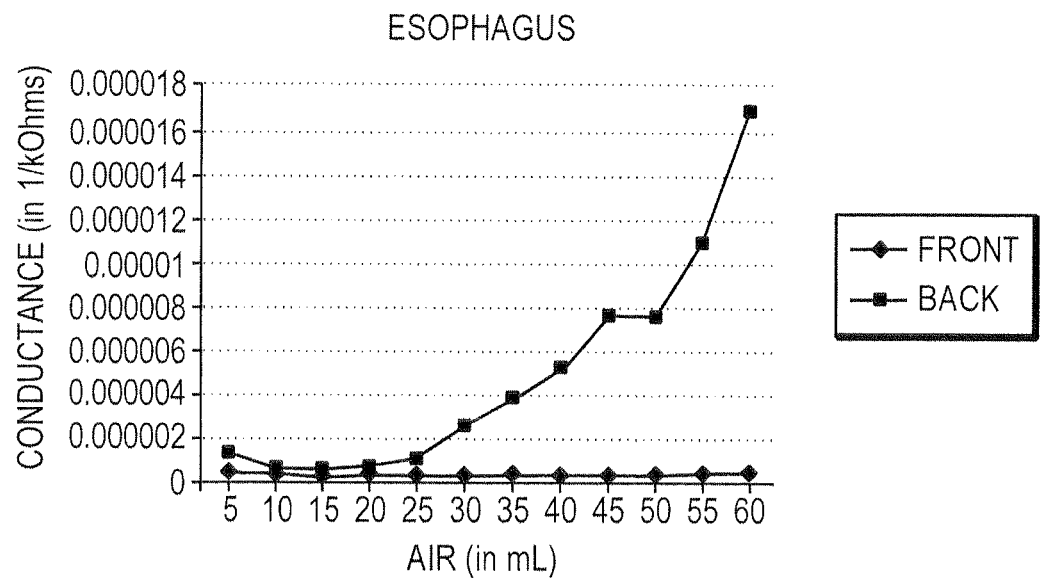
FIGS. 6A and 6B are graphs illustrating measured force as units of conductance used to distinguish an anterior and posterior of an esophagus and trachea, respectively, in pigs.
Figure 6B:
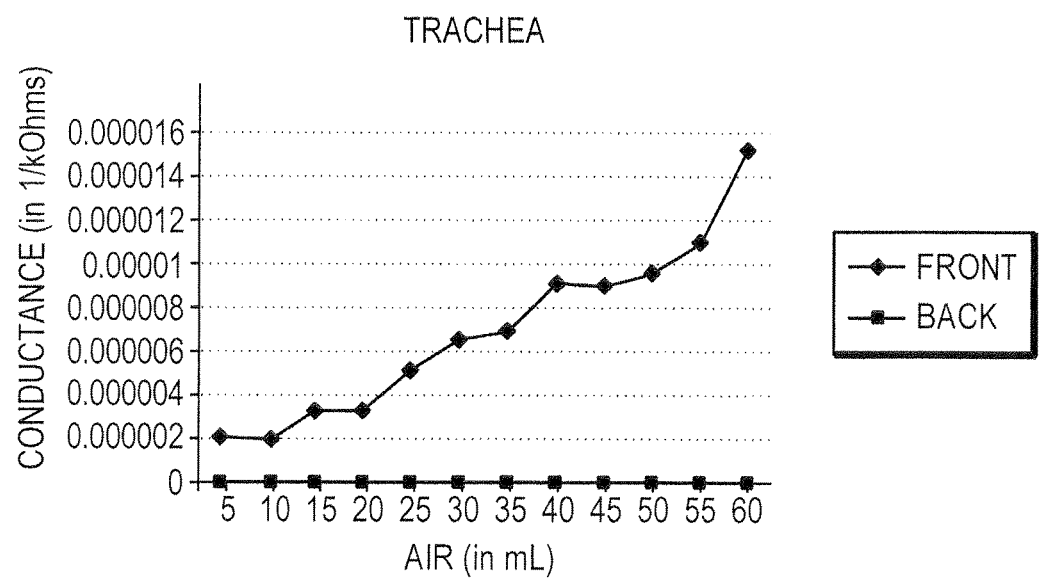
Figure 7:
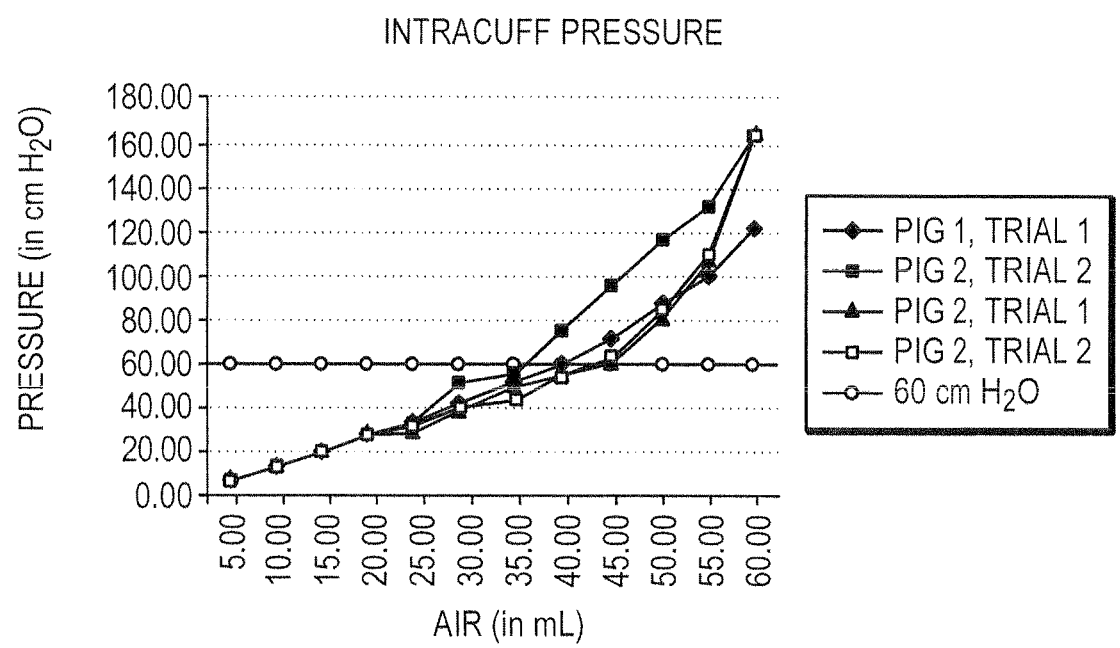
FIG. 7 is a graph illustrating pressure within a cuff as a function of inflation of the cuff and an optimal pressure within the cuff that provides an adequate seal within a lumen of the body for mechanical ventilation.

Experiment 2A—employed each of the designed tubes measuring the forces in the fore and aft sides of the cuff using the Flexiforce piezoresistive force sensors (with the output measured in resistance, but converted to conductance to illustrate force increase) in both the trachea and esophagus. All of the designed tubes were tested by filling their cuffs to their maximal volume; the respective maximum volumes values were as follows: 100 ml and 15 ml for the proximal and distal cuff of the resuscitation tube, 60 ml for the connected cuffs of the transpharyngeal tube, and 20 ml for the single cuff of the endotracheal tube. The results showed that, as volume in milliliters was added into the cuff, the force (recorded in conductance) was higher on the front side (fore) of the cuff in the trachea and the backside (aft) of the cuff in the esophagus (as illustrated in FIG. 6A-6B). In contrast, the force (also recorded in conductance) was lower in the backside of the cuff in the trachea and the front side of the cuff in the esophagus. The intracuff pressure was also measured using a MPX5050 silicon piezoresistive pressure sensor (with output measured in voltage), which increased when air was added to the cuff. The results showed that the recommended optimal pressure was exceeded, as the cuff was filled to maximal inflation (as illustrated in FIG. 7). The optimal pressure under standard conditions (such as no nitrous oxide being used, as this would increase the pressure inside the cuff) is 30 cm H2O for the proximal cuff of the resuscitation tube, 60 cm H2O for the connected cuffs of the transpharyngeal tube, and 34 cm H2O, with the pressure measured at 60+/−15 cm H2O, 140+/−20 cm H2O (FIG. 5B), and 65+/−18 cm H2O, respectively.

Experiment 2B—During Experiment 2B, the electric circuit confirmed proper functioning of pump controller and placement analyzer by the use of output lights that indicate full inflation and placement of the device.

To the extent necessary to understand or complete the disclosure of the present invention, all publications, patents, and patent applications mentioned herein are expressly incorporated by reference therein to the same extent as though each were individually so incorporated.

It should be understood that the methods, as described in reference to or understood with respect to the mechanical, electrical, schematic, or network diagrams, may be implemented in the form of hardware, firmware, or software. In the case of software, the software may be any language capable of performing the example embodiments disclosed herein or equivalents thereof or example embodiments understood in the art at the present time or later developed, or equivalents thereof, as understood from the teachings herein. Moreover, it should be understood that the software may be stored in any form of computer-readable medium, such as Random Access Memory (RAM), Read-only Memory (ROM), Compact-Disk ROM (CD-ROM), optical or magnetic medium, as so forth. The software may be stored thereon as sequences of instructions and loaded and executed by processor(s), including general purpose or application specific processor(s) capable of executing the software in manner(s) disclosed herein or understood from the disclosed embodiments or equivalents thereof.

While this invention has been particularly shown and described with references to example embodiments thereof, it will be understood by those skilled in the art that various changes in form and details may be made therein without departing from the scope of the invention encompassed by the appended claims.

What is claimed is:

1. An intubation device, comprising:
   an intubation tube having a cuff coupled thereto; and
   an intubation aide coupled to the cuff and configured to control a state of the cuff as a function of the cuff's interaction with a lumen of a subject,
   wherein the intubation aide includes a placement analyzer configured to detect which lumen, trachea or esophagus, the intubation tube has been inserted, and to control a state of the cuff as a function of the lumen detected, and wherein the placement analyzer is further configured to calculate a differential between fore and aft pressures of the cuff, a positive differential indicating the intubation tube is located in the trachea and a negative differential indicating the intubation tube is located in the esophagus.

2. The intubation device of claim 1, wherein the intubation aide further includes a notification module configured to notify a medical caregiver into which lumen the tube has been inserted.

3. The intubation device of claim 1, wherein the intubation aide includes a pump, pump controller, and pressure sensor, the pump controller configured to inflate or deflate the cuff as a function of a pressure of the cuff sensed by the pressure sensor.

4. The intubation device according to claim 3 wherein the a placement analyzer is further configured to detect into which lumen the intubation device has been placed and deactivate the pump controller if an incorrect placement is detected.

5. A system for automatically operating an intubation device, the system comprising:
   at least one pressure sensor transducer coupled to at least one cuff coupled to the intubation tube of the intubation device, the at least one pressure sensor transducer configured to measure pressure exerted on a fore, aft, or interior of the at least one cuff based on contact with and pressure exerted by the at least one cuff on an anterior and posterior, respectively, of the trachea or esophagus or internal pressure of the at least one cuff;
   a placement analyzer configured to receive measured forces from the at least one pressure sensor transducer and to signal whether the intubation tube is located in the trachea or esophagus;
   a pump configured to inflate the at least one cuff of the intubation device, positioned within an esophagus or trachea, responsive to an activation signal; and
   a timer configured to selectably generate a deactivation signal to deactivate the inflating or deflate the at least one cuff to enable the intubation tube to be withdrawn from the trachea or esophagus.

6. The system of claim 5, wherein the pressure sensor transducer includes a sensor selected from a group consisting of: fiber optic pressure sensors, pressure transducers, contact sensors, strain sensors, piezoresistive force sensors, interlink force sensing resistors, load cells with piezoelectric crystals, and piezoresistive pressure sensors.

7. The system of claim 5, wherein the placement analyzer is further configured to send a digital readout, light, or sound to the intubation device that indicates whether the intubation tube is located in the trachea or esophagus.

8. The system of claim 5, wherein the placement analyzer is further configured to send a signal to an external device that indicates whether the intubation tube is located in the trachea or esophagus.

9. The system of claim 5 further comprising a control unit configured to respond to controls signals from an external device or control signals initiated at a local human-to-machine interface and further configured to operate the intubation device in response to the control signals.

10. The system of claim 9, wherein the control unit is further configured to perform readiness checks or calibrations in response to the control signals.

11. A system for automatically determining whether an intubation tube of an intubation device is located in a trachea or esophagus, the system comprising:
   at least one pressure sensor transducer coupled to at least one cuff coupled to the intubation tube of the intubation device, the at least one pressure sensor transducer configured to measure pressure exerted on a fore or aft of the at least one cuff based on contact with and pressure exerted by the at least one cuff on an anterior and posterior, respectively, of the trachea or esophagus; and
   a placement analyzer configured to receive measured forces from the at least one pressure sensor transducer and to signal whether the intubation tube is located in the trachea or esophagus, wherein the placement analyzer is further configured to calculate a differential between the fore and aft pressures, a positive differential indicating the intubation tube is located in the trachea and a negative differential indicating the intubation tube is located in the esophagus.

12. A system for automatically determining whether an intubation tube of an intubation device is located in a trachea or esophagus, the system comprising:
   at least one pressure sensor transducer coupled to at least one cuff coupled to the intubation tube of the intubation device, the at least one pressure sensor transducer configured to measure pressure exerted on a fore or aft of the at least one cuff based on contact with and pressure exerted by the at least one cuff on an anterior and posterior, respectively, of the trachea or esophagus; and
   a placement analyzer configured to receive measured forces from the at least one pressure sensor transducer and to signal whether the intubation tube is located in the trachea or esophagus, wherein the placement analyzer is further configured to compare either the fore or aft pressures with an absolute threshold, the comparison indicating whether the intubation tube is located in the trachea or esophagus.

13. A system for automatically operating an intubation device, the system comprising:
   at least one pressure sensor transducer coupled to at least one cuff coupled to the intubation tube of the intubation device, the at least one pressure sensor transducer configured to measure pressure exerted on a fore, aft, or interior of the at least one cuff based on contact with and pressure exerted by the at least one cuff on an anterior and posterior, respectively, of the trachea or esophagus or internal pressure of the at least one cuff;
   a placement analyzer configured to receive measured forces from the at least one pressure sensor transducer and to produce an activation signal indicating whether the intubation tube is located in the trachea or esophagus;
   a pump configured to inflate the at least one cuff responsive to an activation signal; and
   a pump controller configured to:
      monitor the inflation of the at least one cuff
      generate a deactivation signal as a function of a level of the inflation; and
      cause the pump to discontinue inflation of or deflate the at least one cuff responsive to the deactivation signal.

14. A method for determining whether an intubation tube of an intubation device is located in a trachea or esophagus, the method comprising:
   measuring pressures exerted on a fore, aft, or interior of at least one cuff coupled to the intubation tube following at least partial inflation of the at least one cuff based on contact with an anterior and posterior, respectively, of the trachea or esophagus or internal pressure of the at least one cuff;
   determining whether the intubation tube is located in the trachea or esophagus as a function of the pressures;
      signaling whether the intubation tube is located in the trachea or esophagus;
      inflating the at least one cuff of the intubation device, positioned within an esophagus or trachea, responsive to an activation signal; and
   selectably including generating a deactivation signal to deactivate the inflating or deflate the at least one cuff to enable the intubation tube to be withdrawn from the trachea or esophagus.

15. The method of claim 14, wherein at least one pressure sensor transducer is used to measure the pressure exerted on the fore of the at least one cuff, aft of the at least one cuff, or both.

16. The method of claim 15, wherein the pressure sensor transducer is a piezoelectric transducer.

17. The method of claim 14, wherein the pressures are measured using at least one of the following: fiber optic pressure sensors, pressure transducers, contact sensors, and strain sensors.

18. The method of claim 14, wherein signaling further includes sending a signal to the intubation device that indicates whether the intubation tube is located in the trachea or esophagus.

19. The method of claim 14, wherein signaling further includes sending a signal to an external device that indicates whether the intubation tube is located in the trachea or esophagus.

20. The method of claim 14 further comprising comparing either the fore or aft pressures with an absolute threshold, the comparison indicating whether the intubation tube is located in the trachea or esophagus.

21. The method of claim 14 further comprising:
   commencing inflation of the at least one cuff responsive to an activation signal;
   monitoring the inflation of the at least one cuff;
   generating a deactivation signal as a function of a level of the inflation; and
   discontinuing inflation of or deflating the at least one cuff responsive to the deactivation signal.

22. The method of claim 14 further comprising responding to controls signals from an external device or from a local human-to-machine interface and operating the intubation device in response to the control signals.

23. The method of claim 22, wherein responding to control signals includes performing readiness checks or calibrations in response to the control signals.

24. A method for determining whether an intubation tube of an intubation device is located in a trachea or esophagus, the method comprising:
   measuring pressures exerted on a fore or aft of at least one cuff coupled to the intubation tube following at least partial inflation of the at least one cuff based on contact with an anterior and posterior, respectively, of the trachea or esophagus;
   determining whether the intubation tube is located in the trachea or esophagus as a function of the pressures by calculating a differential between the fore and aft pressures, a positive differential indicating the intubation tube is located in the trachea and a negative differential indicating the intubation tube is located in the esophagus; and signaling whether the intubation tube is located in the trachea or esophagus.

25. A system for controlling inflation of at least one cuff coupled to an intubation tube of an intubation device, the system comprising:

a pump configured inflate the at least one cuff responsive to an activation signal;

a pump controller configured to:
monitor the inflation of the at least one cuff;
generate a deactivation signal as a function of a level of the inflation; and
discontinue inflation of or deflate the at least one cuff responsive to the deactivation signal, wherein the pump controller includes a timer, the timer configured to generate the deactivation signal after an elapsed time.

26. The system of claim 25, wherein the level of inflation is determined by a desired pressure, force, or volume of the at least one cuff.

27. The system of claim 26, wherein the desired pressure, force, or volume of the at least one cuff is a pressure, force, or volume that provides a seal between the at least one cuff and walls of the trachea or esophagus without excess pressure or force applied to the walls of the trachea or esophagus with a suitable airway for ventilation using the intubation device being maintained.

28. The system of claim 25, wherein the pump controller is further configured to:
determine a maximal pressure of the at least one cuff; and
if the pressure of the at least one cuff is beyond the maximal pressure, deflate the at least one cuff to return to the maximal pressure.

29. The system of claim 25, wherein the elapsed time is a time chosen by a user of the intubation device expected to fill the at least one cuff to a specific volume as a function of an output of the pump used to inflate the at least one cuff.

30. The system of claim 25, wherein the at least one cuff is inflated with a gas or fluid.

31. The system of claim 25 further comprising:
at least one pressure sensor transducer coupled to the at least one cuff coupled to the intubation tube of the intubation device, the at least one pressure sensor transducer configured to measure pressure exerted on a fore or aft of the least one cuff as a function of contact with an anterior or posterior of a trachea or esophagus; and a placement analyzer configured to receive measured pressures from the at least one pressure sensor transducer and to signal whether the intubation tube is located in the trachea or esophagus.

32. A method for controlling inflation of at least one cuff coupled to an intubation tube of an intubation device, the method comprising:
inflating the at least one cuff responsive to an activation signal;
monitoring the inflation of the at least one cuff;
generating a deactivation signal as a function of a level of the inflation;
discontinuing inflation of or deflating the at least one cuff responsive to the deactivation signal,
wherein generating the deactivation signal further includes generating the deactivation signal after an elapsed time, the elapsed time being a time chosen by a user of the intubation device expected to fill the at least one cuff to a specific volume as a function of an output of a pump used to fill the at least one cuff.

33. The method of claim 32, wherein the level of inflation is determined by a desired pressure, force, or volume of the at least one cuff.

34. The method of claim 33, wherein the desired pressure, force, or volume of the at least one cuff is a pressure, force, or volume that provides a seal between the at least one cuff and walls of the trachea or esophagus without excess pressure or force applied to the walls of the trachea or esophagus such that a suitable airway for ventilation using the intubation device is maintained.

35. The method of claim 32 further comprising:
determining a maximal pressure of the at least one cuff and if the pressure of the at least one cuff is beyond the maximal pressure, deflating the at least one cuff to return to the maximal pressure.

36. The method of claim 32, wherein inflating the at least one cuff includes inflating the at least one cuff with a gas or fluid.

37. The method of claim 32 further comprising:
measuring pressures exerted on a fore or aft of the at least one cuff, coupled to the intubation tube following at least partial inflation of the at least one cuff as a function of pressure exerted by the at least one cuff on an anterior or posterior, respectively, of a trachea or esophagus;
determining whether the intubation tube is located in the trachea or esophagus as a function of the pressures measured; and
signaling whether the intubation tube is located in the trachea or esophagus.

* * * * *